US012788271B2

(12) United States Patent
Cadwell et al.

(10) Patent No.: US 12,788,271 B2
(45) Date of Patent: Nov. 10, 2026

(54) METHODS AND SYSTEMS FOR MONITORING CIRCUMFERENTIAL OR LINEAR DISPLACEMENTS TO DETERMINE RESPIRATORY ACTIVITY

(71) Applicant: Cadwell Laboratories, Inc., Kennewick, WA (US)

(72) Inventors: John A. Cadwell, Richland, WA (US); John A. Cadwell, Jr., Richland, WA (US); David John Yarger, Kennewick, WA (US); Colton Wallin, Pasco, WA (US)

( * ) Notice: Subject to any disclaimer, the term of this patent is extended or adjusted under 35 U.S.C. 154(b) by 1023 days.

(21) Appl. No.: 17/819,132

(22) Filed: Aug. 11, 2022

(65) Prior Publication Data

US 2023/0048642 A1 Feb. 16, 2023

Related U.S. Application Data

(60) Provisional application No. 63/260,211, filed on Aug. 12, 2021.

(51) Int. Cl.

*A61B 5/08* (2006.01)
*A61B 5/00* (2006.01)
*A61B 5/0522* (2021.01)

(52) U.S. Cl.

CPC .......... *A61B 5/0806* (2013.01); *A61B 5/0522* (2013.01); *A61B 5/6831* (2013.01)

(58) Field of Classification Search

CPC ... A61B 5/0806; A61B 5/0522; A61B 5/6831; A61B 5/1135

See application file for complete search history.

(56) References Cited

U.S. PATENT DOCUMENTS 4,308,872 A 1/1982 Watson
4,631,478 A * 12/1986 Knetsch ............... G01D 5/2006 336/20
4,817,625 A 4/1989 Miles
5,331,968 A 7/1994 Williams
6,275,131 B1 8/2001 Swope
6,461,307 B1 10/2002 Kristbjarnarson
7,390,307 B2 6/2008 Eriksen
8,007,443 B2 8/2011 Newman
8,019,401 B1 9/2011 Smith
8,025,539 B2 9/2011 Hermannsson
8,034,001 B2 10/2011 Gal
(Continued)

OTHER PUBLICATIONS

Zyga. "Spandex manufacturer makes elastic electrical cable." https://phys.org/news/2011-12-spandex-elastic-electrical-cable-video.html. phys.org, Dec. 2, 2011.
(Continued)

*Primary Examiner* — Stephen D Meier
*Assistant Examiner* — Quang X Nguyen
(74) *Attorney, Agent, or Firm* — Novel IP

(57) ABSTRACT

A respiratory monitoring system that uses an elastic cord with at least one wire wound around the elastic cord such that, when current passes through, it generates a magnetic field along the length of the elastic cord. The system further includes a recorder that measures changes in inductance and/or frequency in order to derive a respiratory rate of a patient in a coil cord. Embodiments of the system of the present specification have application in Respiratory Inductive Plethysmography (RIP) belts.

20 Claims, 17 Drawing Sheets

500a

(56) References Cited

U.S. PATENT DOCUMENTS

| | | | | |
|---|---|---|---|---|
| 8,052,612 | B2 | 11/2011 | Tang | |
| 8,251,736 | B2 | 8/2012 | Mcintire | |
| 8,294,029 | B2 | 10/2012 | Tatsumi | |
| 8,323,219 | B2 | 12/2012 | Cochran | |
| 8,693,829 | B2 | 4/2014 | Tatsumi | |
| 8,969,724 | B2 | 3/2015 | Tatsumi | |
| 9,455,072 | B2 | 9/2016 | Tatsumi | |
| 10,141,675 | B2 | 11/2018 | Hermannsson | |
| 2013/0085538 | A1* | 4/2013 | Volpe | A61B 5/1135<br>607/6 |
| 2015/0097806 | A1* | 4/2015 | Jeong | G06F 3/0446<br>345/174 |
| 2021/0085242 | A1* | 3/2021 | Hoskuldsson | A61B 5/0806 |
| 2023/0172473 | A1* | 6/2023 | Ojarand | A61B 5/277<br>600/301 |

OTHER PUBLICATIONS

Montazeri et al. "The design of RIP belts impacts the reliability and quality of the measured respiratory signals." Sleeping and Breathing, Jan. 7, 2021; https://doi.org/10.1007/s11325-020-02268-x.

Medhurst. "H.F. Resistance and Self-Capacitance of Single-Layer Solenoids." Wireless Engineer, Feb. 1947.

L.G. Dobbie, M.E., "Calcuation of Inductance"; Radiotron Designer's Handbook Fourth Edition (P. Langford Smith) 1953.

* cited by examiner

METHODS AND SYSTEMS FOR MONITORING CIRCUMFERENTIAL OR LINEAR DISPLACEMENTS TO DETERMINE RESPIRATORY ACTIVITY

CROSS-REFERENCE

The present application relies on U.S. Patent Provisional Application No. 63/260,211, titled "Methods and Systems for Monitoring Circumferential or Linear Displacements to Determine Respiratory Activity" and filed on Aug. 12, 2021, for priority, which is herein incorporated by reference in its entirety.

FIELD

The present specification relates to monitoring a circumferential or linear displacement, which is of particular value in monitoring the respiration of a living animal. More specifically, embodiments of the present specification relate to methods and systems for measuring respiratory activity by monitoring physical displacements of a respiratory inductance plethysmography belt.

BACKGROUND

There are many healthcare applications which require the reliable monitoring of a living being's respiration. For example, to evaluate a person for a sleep disorder, the person's respiration must be monitored over a long period of time. This is typically done using sensors that measure breathing and the expansion of the person's chest and/or abdomen. Such sensors may include air pressure sensors, air temperature sensors, snore sensors, body movement sensors, pulse oximeters, electroencephalograms, and electrocardiograms, among other types of sensors.

Reliable measurements, however, often require the use of respiratory plethysmography which evaluates pulmonary ventilation by measuring the actual physical movement of the person's chest and abdominal walls. In some prior art embodiments, the actual physical movement of the person's chest and abdominal wall is monitored by having an elastic belt around the chest and a second elastic belt around the abdomen. Each belt incorporates a sensor whose output changes when the belt is stretched as a result of the person's respiratory effort that results in relative changes in the users thoracic and abdomen volume. Such belts comprise a stretchable or elastic material having integrated therein, at each end of the belt, a single force or displacement sensor, such as a piezoelectric sensor or strain gauge. However, using a single centrally located sensor is problematic in that the person's respiratory movement may not be reliably transmitted to the sensor, which is frequently the case when the wearer is in prone position. These belts do not have a sensing means that completely encircles the person being monitored or that necessarily experience circumferential or linear displacement occurring some distance away from the sensing means.

The prior art does disclose belts having a planar wire extending circumferentially around the person being monitored. A controller passes current through the wire and the inductance of the system is monitored. The dynamic stretching of the belt, resulting from changes in the person's thoracic or abdominal radius, creates waveforms due to changes in self-inductance and oscillatory frequency of the electronic signal. Therefore, with such belts, the entire belt functions as a sensor since a change in length of any section of the belt affects the measurement in proportion to the magnitude of change and length of the belt.

FIG. 1A illustrates a typical application of such an inductive planar wire sensor. The sensor is configured and is in the form of a respiratory inductance plethysmography (RIP) belt 102 that is worn by a wearer 104 so that it encircles the wearer's body. A recorder 106 is connected to the belt 102. The recorder 106 contains an oscillator and recording system. The wires in the planar RIP belt 102 expand with the belt 102. For a single coil, the inductance increases as the circumference increases. Accordingly, changes in circumference can be measured based on the measured inductance changes. A resonant electronic oscillator, which has a frequency that varies with inductance, is used. The frequency is measured periodically, wherein changes in the frequency between measurements is calculated and the respiratory effort is calculated as a function of the change in frequency. While the wire is generally planar, a zig-zag pattern 600*a* may be added to the design of belt 102 that allows the wire to expand, as shown in FIG. 6A. The zig-zag pattern 600*a* increases the inductance of the belt 102 but reduces its sensitivity. The sensitivity reduces as a result of opposing magnetic fields created by electric current passing through a loop of the zig zag pattern 600*a*. It should be appreciated that, while the wire may be planar or adopt a zig-zag pattern 600*a*, in all known conventional approaches, the magnetic field generated from the electrical current passing through the wire extends normal to the circumference of the belt and parallel to the person's axis extending from the person's head to toe and abstracted by considering the approximate cylinder formed by the thoracic and abdominal regions of the person being monitored.

Unfortunately, because the magnetic field is directed parallel to the axis extending from the person's head to toe, it is subject to destructive effects if the belt is looped upon itself or if two belts are used in proximity to each other. Stated differently, a conductor in a planar RIP belt 102 must carry the current in such a way as to not create a destructive or counteracting magnetic field with any other RIP belt or any portion of the same RIP belt. This results in several critical disadvantages. First, this kind of RIP belt 102 must exactly fit the wearer with each single loop of wire used in belt 102 being terminated at each end. This requires either a) cutting the RIP belt to length and making connections for each use, b) having a large number of belts of different lengths, or c) tucking the excess length through some tortuous configurations. In each case, the procedure is made more complex, prone to error, or subject to excessive signal degradation. Second, it limits the ability to use more than one RIP belt in close proximity with each other, because the RIP belts may destructively cancel each other's magnetic fields. More specifically, when two RIP belts are used, for example an abdominal belt and a thoracic belt, there can be a field-destructive interaction if the two RIP belts are in approximately the same plane or encircle the magnetic field axis, common to the two RIP belts, extending through the core of the wearer. Current state of the art, if employing two planar RIP belts, may need to operate each of the two belts at a different excitation frequency or with interleaved timing to mitigate this destructive, noisy interference. Third, the patient is exposed to the radio frequency electromagnetic field generated by the coil.

Therefore, there is a need to develop improved methods and systems for measuring linear or circumferential displacements that are not susceptible to the aforementioned destructive interference limitations. There is also a need to develop improved methods and systems for accurately measuring respiration that a) is sensitive to pulmonary or abdominal volume changes anywhere around the torso of the person being monitored, b) is not susceptible to destructive interface if portions of the belt is looped upon itself, c) is not susceptible to destructive interface if more than one belt is used in proximity to each other, d) is simpler to use and more reliable for the end user, e) reduces radio frequency exposure to the patient, e) provides good signal quality even if the active portion of the sensing coil does not completely surround the patient or if the active portion of the sensing coil overlaps on itself.

SUMMARY

The following embodiments and aspects thereof are described and illustrated in conjunction with systems, tools and methods, which are meant to be exemplary and illustrative, and not limiting in scope. The present application discloses numerous embodiments.

The present specification discloses a respiratory monitoring system, comprising: a cord configured to extend around a torso of a person, wherein the cord comprises: a core member comprising an elastic material, wherein the core member is defined by a length and wherein the elastic material is configured to stretch from a first length to a second length, when a force is applied thereto and; and at least one helical conductive coil positioned around the core member, wherein the at least one helical conductive coil is adapted to generate a magnetic field substantially parallel to the length of the core when electric current having a predefined frequency is passed through the at least one helical conductive coil; an electrical current source in electrical communication with the at least one helical conductive coil and adapted to generate said electric current; a sensor electrically coupled to the at least one helical conductive coil and configured to measure a change in at least one of an inductance of the at least one helical conductive coil or the frequency of electrical current in the at least one helical conductive coil; and a controller coupled to the sensor and configured to receive data indicative of said measured change and determine a respiration value based on said data.

Optionally, the second length is at least 10% greater than the first length.

Optionally, the cord comprises a second helical conductive coil positioned parallel to the at least one helical conductive coil and wrapped around the core member, and wherein the first helical conductive coil is electrically insulated from the second helical conductive coil.

Optionally, a first magnetic field generated by a first loop of the first helical conductive coil and a second magnetic field generated by a second loop of the first helical conductive coil are more additive in intensity than destructive in intensity.

Optionally, the at least one helical conductive coil is wrapped in a casing configured to prevent a surface of the at least one helical conductive coil from directly contacting a user's skin.

Optionally, the at least one helical conductive coil comprises windings having a density in a range of 10 to 20 turns per inch and wherein the at least one helical conductive coil comprises a wire in a range of 20 to 40 gauge.

Optionally, the at least one helical conductive coil comprises windings having a density in a range of 1 turn per inch to 50 turns per inch using a wire having a gauge in a range of 10 to 50 and wherein the core member has a diameter in a range of 0.01 inch to 4 inches.

Optionally, the cord is disposed on a flat carrier to form a web. Optionally, the web comprises a second cord wherein the second cord comprises a second helical conductive coil wound around a second core member, and wherein the second helical conductive coil is adapted to generate a magnetic field extending along a length of the second core member when electric current having a predefined frequency is passed through the second helical conductive coil. Optionally, the web is shaped as a flat, curved, or tubular surface. Optionally, the cord is centered in a cross section of the web, positioned on an exterior surface of the web or positioned in a perimeter of the web. Optionally, the web comprises a connector that mechanically connects a first end of the web to a second end of the web when the web is encircled around the torso.

Optionally, a first portion of the cord extends along one direction on the core member and a second portion of the cord extends along a second opposing direction on the core member creating a return loop, wherein a free end of the first and the second portions are aligned at a same end of the core member.

Optionally, the electrical current source comprises an oscillator configured to generate the electric current having the predefined frequency.

The present specification also discloses a method of monitoring a respiration rate of a person, comprising: positioning a respiratory inductance plethysmography belt around a torso of a person wherein the respiratory inductance plethysmography belt comprises a carrier having a cord positioned thereon, wherein the cord comprises a core member made of an elastic material, wherein the core member is defined by a length and wherein the elastic material is configured to stretch from a first length to a second length in a direction parallel to a ground level when the person is standing and when a force is applied thereto and at least one helical conductive coil positioned around the core member, wherein the at least one helical conductive coil is adapted to generate a magnetic field substantially parallel to the length of the core when electric current having a predefined frequency is passed through the at least one helical conductive coil; activating an electrical current source in electrical communication with the at least one helical conductive coil to generate said electric current; activating a sensor electrically coupled to the at least one helical conductive coil; using the sensor, measuring a change in at least one of an inductance of the at least one helical conductive coil or the frequency of electrical current in the at least one helical conductive coil; and determining a respiration value based on the measured change in the inductance or the frequency.

Optionally, the cord comprises a second helical conductive coil positioned parallel to the at least one helical conductive coil and wound around the core member.

Optionally, the at least one helical conductive coil comprises windings having a density in a range of 10 to 20 turns per inch and wherein the at least one helical conductive coil comprises a wire in a range of 20 to 40 gauge.

Optionally, the carrier comprises a second extensible cord and wherein the second extensible cord comprises a second helical conductive coil wound around a second core member and wherein the second helical conductive coil is adapted to generate a magnetic field extending along a length of the second elastic core when electric current having a predefined frequency is passed through the second helical conductive coil.

Optionally, the carrier comprises a web having a mechanical connector that connects a first end of the web to a second end of the web when the web is encircled around the torso.

Optionally, the electrical current source comprises an oscillator configured to generate the electric current having the predefined frequency.

In some embodiments, the present specification discloses a respiratory monitoring system, comprising: an extensible cord configured to extend around a torso of a person, wherein the extensible cord comprises: an elastic core; and single or double conductive helical coil wound around the elastic core, wherein the conductive helical coil is adapted to generate a magnetic field extending along a length of the elastic core when electric current having a predefined frequency is passed through the conductive helical coil; an electrical current source in electrical communication with the conductive helical coil and adapted to generate said electric current; a sensor electrically connected to the conductive helical coil and configured to measure a change in at least one of an inductance of the conductive helical coil or the frequency of electrical current in the conductive helical coil; and a controller configured to determine a respiration value based on the measured change in the inductance or the frequency.

Optionally, the double helix conductive coil comprises a first helix defined by windings having a density in a range of 10 to 20 turns per inch and a wire in a range of 20 to 40 gauge and a second helix overlapping the first helix and defined by windings having a density in a range of 10 to 20 turns per inch and a wire in a range of 20 to 40 gauge. Optionally, the second helix is wound in the opposite direction to the first helix.

Optionally, a single helix conductive coil comprises a helix defined by windings having a density in a range of 10 to 20 turns per inch and a wire in a range of 20 to 40 gauge, wherein the cord goes out and back in a single loop along a supporting elastic belt.

Optionally, the extensible cord is disposed on a flat carrier to form a web.

Optionally, the web comprises a mechanical connector that connects a first end of the web to a second end of the web when the web is encircled around the torso.

Optionally, the electrical current source comprises an oscillator configured to generate the electric current having the predefined frequency.

In some embodiments, the present specification discloses a method of monitoring a respiration rate of a person, comprising: positioning a respiratory inductance plethysmography belt around a torso of a person wherein the respiratory inductance plethysmography belt comprises a carrier having an extensible cord positioned thereon, wherein the extensible cord comprises an elastic core and a helical coil wound around the elastic core, wherein the helical coil is adapted to generate a magnetic field extending along a length of the elastic core when electric current having a predefined frequency is passed through the helical coil; activating an electrical current source in electrical communication with the helical coil to generate said electric current; activating a sensor electrically connected to the helical coil; using the sensor, measuring a change in at least one of an inductance of the helical coil or the frequency of electrical current in the helical coil; and determining a respiration value based on the measured change in the inductance or the frequency.

In some embodiments, the present specification discloses an inductor encirclement assembly for monitoring respiratory cycle, said assembly comprising: an inductor web configured to extend around a torso of a person, wherein the inductor web comprises: a carrier configured with a cleat for accepting the inductor web and enabling the inductor web to encircle the torso of the person; and a helical coil wound around the carrier, wherein the helical coil is adapted to generate a magnetic field extending along a length of the inductor web when an electric current having a predefined frequency is passed through the helical coil; wherein the inductor web is connected to a connection housing comprising electrical connections connecting with a single-point electrical wire; an electrical current source in electrical communication with the single-point electrical wire and adapted to generate said electric current; a sensor electrically connected to the helical coil and configured to measure a change in at least one of an inductance of the double helix conductive coil or the frequency of electrical current in the helical coil; and a controller configured to determine a respiration value based on the measured change in the inductance or the frequency.

Optionally, the cleat is a spring cleat adapted to accept a tag end of the inductor web to hold said end in a desired position.

Optionally, the cleat is coupled with the carrier and positioned adjacent to the connection housing.

Optionally, the cleat is configured on an external surface of the connection housing, and wherein the external surface is opposite to an internal surface that faces a body volume of the person using inductor web.

In some embodiments, the present specification discloses a respiratory monitoring system, comprising: an extensible cord configured to extend around a torso of a person, wherein the extensible cord comprises: an elastic core; and at least one helical conductive coil wound around the elastic core, wherein the at least one helical conductive coil is adapted to generate a magnetic field extending along a length and axis of the elastic core when electric current having a predefined frequency is passed through the at least one helical conductive coil; an electrical current source in electrical communication with the at least one helical conductive coil and adapted to generate said electric current; a sensor electrically connected to the at least one helical conductive coil and configured to measure a change in at least one of an inductance of the at least one helical conductive coil or the frequency of electrical current in the at least one helical conductive coil; and a controller configured to determine a respiration value based on the measured change in the inductance or the frequency.

In some embodiments, the present specification discloses a method of monitoring a respiration rate of a person, comprising: positioning a respiratory inductance plethysmography belt around a torso of a person wherein the respiratory inductance plethysmography belt comprises a carrier having an extensible cord positioned thereon, wherein the extensible cord comprises an elastic core and at least one helical conductive coil wound around the elastic core, wherein the at least one helical conductive coil is adapted to generate a magnetic field extending along a length of the elastic core when electric current having a predefined frequency is passed through the at least one helical conductive coil; activating an electrical current source in electrical communication with the at least one helical conductive coil to generate said electric current; activating a sensor electrically connected to the at least one helical conductive coil; using the sensor, measuring a change in at least one of an inductance of the at least one helical conductive coil or the frequency of electrical current in the at least one helical conductive coil; and determining a respiration value based on the measured change in the inductance or the frequency.

The aforementioned and other embodiments of the present specification shall be described in greater depth in the drawings and detailed description provided below.

BRIEF DESCRIPTION OF THE DRAWINGS

The accompanying drawings illustrate various embodiments of systems, methods, and embodiments of various other aspects of the disclosure. Any person with ordinary skills in the art will appreciate that the illustrated element boundaries (e.g. boxes, groups of boxes, or other shapes) in the figures represent one example of the boundaries. It may be that in some examples one element may be designed as multiple elements or that multiple elements may be designed as one element. In some examples, an element shown as an internal component of one element may be implemented as an external component in another and vice versa. Furthermore, elements may not be drawn to scale. Non-limiting and non-exhaustive descriptions are described with reference to the following drawings. The components in the figures are not necessarily to scale, emphasis instead being placed upon illustrating principles.

DETAILED DESCRIPTION

Figure 1A:
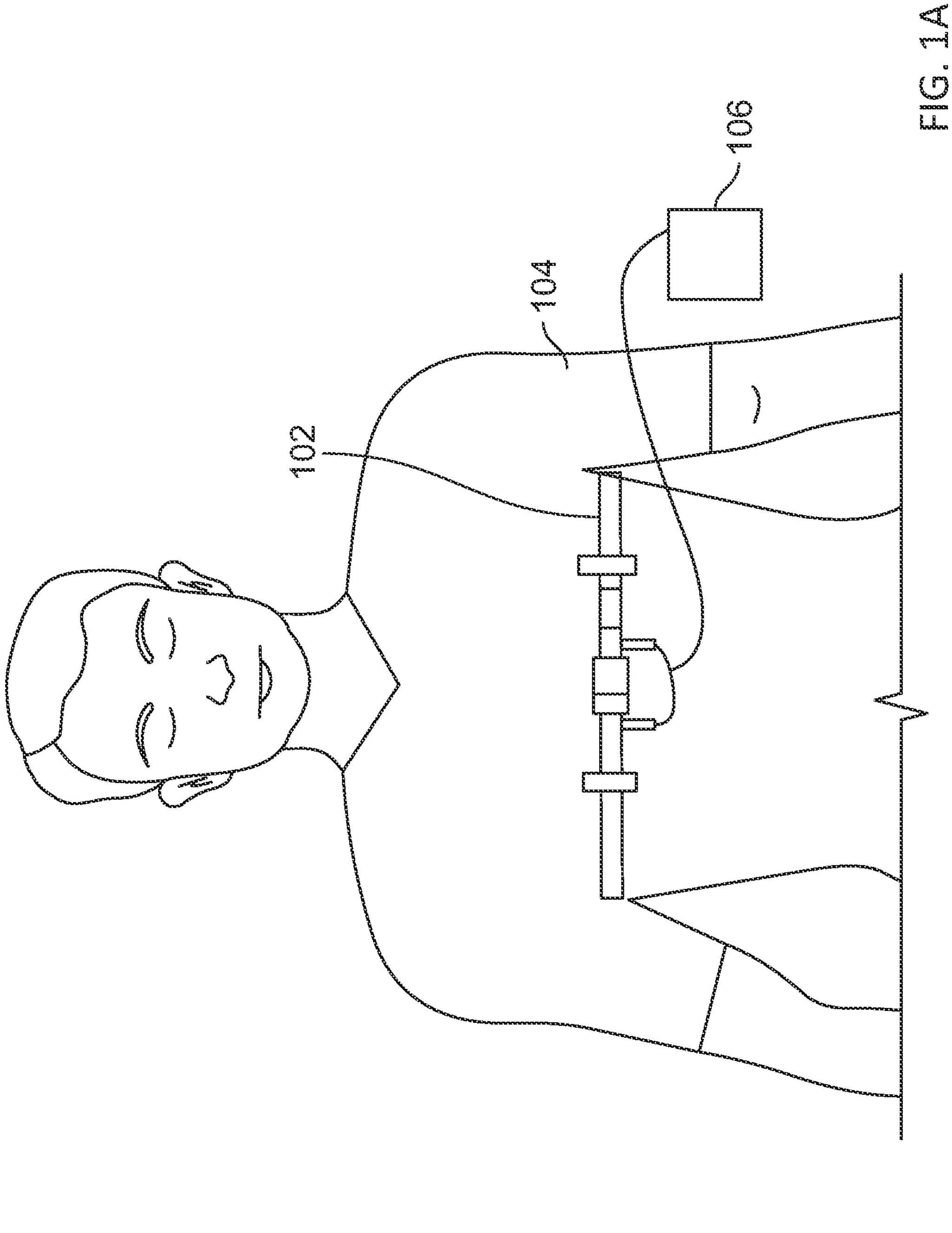
FIG. 1A (PRIOR ART)
FIG. 1A illustrates a typical application of a prior art RIP belt.

The present specification is directed toward methods and systems suitable for monitoring circumferential or linear displacements. Embodiments of the present specification have a preferred use in respiratory inductance plethysmography (RIP). The RIP cord of the present specification is configured with a geometric arrangement of wire in a helical form that, when an electrical current is passed therethrough, generates a magnetic field described by a vector tangential to a circumference, assuming the belt is positioned around the torso of a person, or along a straight axis, assuming the belt is positioned on a flat surface. The windings of the RIP belt are wrapped helically around an elastic cord, thus the RIP belt functions as an elastic coil inductor or an elastic helical inductor. In various embodiments, the helical winding or helical form should be thought of as a coil of wire. In some embodiments, the cord is extensible and comprises a round cord. In some embodiments, the cord is the result of a fabrication of a supporting band, for example, from an elastic band weaving machine, and has an equivalent cross section as a single round cord. In other embodiments, the extensible cord is not included and the required cross section of the belt is maintained by the rigidity of coil wires included in the belt. In some embodiments, the extensible cord has magnetic properties. In other embodiments, the cord does not have magnetic properties.

In some embodiments, the belt comprises double helical coils. In some double helical coil embodiments, first and second helical coils are wound in the same direction. In some double helical coil embodiments, a second coil is wound in an opposite direction to the winding of a first coil. In some embodiments, the belt comprises a single helical coil. In single helical coil embodiments, the outgoing and returning sections are spaced apart from each other, preferably by more than 3 diameters of helical coil.

In various embodiments, belts comprising either single or double helical coils comprise a first helix as described and a return wire in any configuration that is extensible without necessarily having a helical configuration. In some embodiments, the return wire has a planar configuration.

Single helical designs and double helical designs utilize the same strategy of maintaining the magnetic field primarily along the axis of the coil rather than primarily along the head-toe axis of the patient. Except as noted, the term ‘helical coil’ refers to both the single helix conductive coil and the double helix conduction coil.

In various embodiments of the present specification, a double coil within the physical constraint space considered is approximately 1.8 times more sensitive than a single coil. When compared to typical planar embodiments, the disclosed extensible coil embodiments are approximately 2 to 10 times more sensitive in terms of inductance change per breathing cycle for a RIP embodiment. In various embodiments, the double helix configuration has a significantly higher inductor quality than the single helix embodiment. Embodiments of the present specification have higher inductor quality factors than existing planar embodiments, allowing for better performance considering a whole measurement system.

The orientation of the magnetic field created by the RIP belt of the present specification is along the cord in contrast to conventional planar coils where the primary magnetic field is at right angles to the coil and along the axial length of the person. More specifically, and as further discussed in relation to FIGS. 3B and 5B, the generated magnetic field is directed either clockwise or counterclockwise along each helical winding and, when summed, constructively results in a magnetic field extending in the same direction as the length of the elastic cord around which the helical windings are wrapped. This effect is additive even if the RIP belt is looped around itself or if a second RIP belt is positioned proximate the first RIP belt, assuming proper electrical current flow. If two conventional planar inductive belts are employed then each of the belts may need to be operated at a different excitation frequency to mitigate the combined destructive, noisy interference. The RIP belt of the present specification removes this problem through a change in the axis of magnetism (along the circumference of the inductor coil cord) which precludes the magnetic fields of two inductive belts from intersecting with each other, In some cases, this further leads to foolproof electronics, defined as electronics that may not require circuitry or design to deal with inductors working around the same magnetic axis.

Figure 1B:
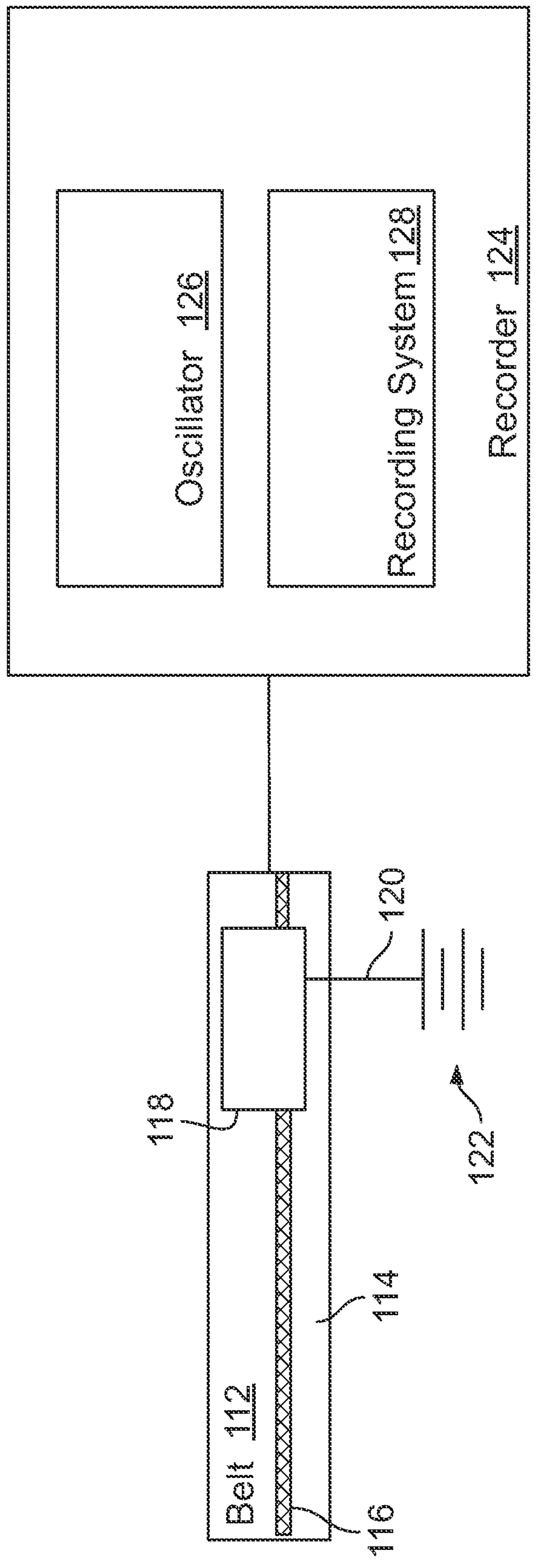
FIG. 1B illustrates an application of an inductive planar wire sensor in accordance with some embodiments of the present specification.

FIG. 1B illustrates an application of an inductive planar wire sensor in accordance with some embodiments of the present specification. The sensor is in the form of an RIP belt 112 that is worn by a wearer so that it encircles the wearer’s body. In some embodiments, the belt is formed with an inductor web 114 that comprises an inductor coil cord 116. In embodiments, coil cord 116 is a single or double helix inductor coil cord. Coil cord 116 is attached to planar surface of inductor web 114 of belt 112, and expands with the belt 112. For a single helical coil cord 116, the inductance decreases as the windings of the helix move farther apart as circumference increases. Exemplary configurations of coil cord 116 are described subsequently in FIGS. 6B, 6C, and 6D. Accordingly, changes in circumference can be measured based on the measured inductance changes. The inductor web 114 is connected to a connection housing 118 that houses electrical connections and further connects with a single-point electrical wire 120 that connects to a power supply 122. In some embodiments, power supply 122 source is a battery. Connection housing 118 may also include a tag end where inductor web 114 loops to encircle a body volume.

It should be appreciated that while, in some embodiments, the RIP belt 112 is formed with the inductor web 114, in alternate embodiments the inductor coil cord 116 may function without an inductor web. For example, the coil cord could entirely be cylindrical.

Additionally, a recorder unit 124 is connected to the connection housing 118. In some embodiments, the recorder unit 124 is configured within housing 118 or is electrically connected by a wire to housing 118. Recorder unit 124 contains an oscillator 126 and a recording system 128. In some embodiments, a resonant electronic oscillator 126 is used whose frequency varies with inductance. The frequency is measured periodically. Changes in the frequency between measurements is calculated and the respiratory effort is calculated as a function of the change in frequency. The measurements are recorded by recording system 128. In some embodiments, additional electronic components within recorder unit 124 convert analog information measured by oscillator 126 into digital analyzable information.

It should be appreciated that the present invention includes the computing device, electrical circuitry, and/or controller hardware that are in electrical communication with the helical windings described herein and required to a) generate an oscillating electrical current in accordance with a predefined frequency, b) measure the inductance and/or measure the frequency changes which occur during use, and c) determine from the measured changes in inductance and/or frequency (caused by the expansion or contraction of the helical windings relative to each other and induced by the generated magnetic fields) the degree of movement and, accordingly, the respiration rate of the person being monitored.

In embodiments, the inductance and sensitivity to stretch is controlled by choice of wire size, cord diameter, winding spacing and winding geometry, which together form the helix. The inductance is integral to all the helical windings. As the cord is stretched, windings of the helix move farther apart resulting in a decrease in the inductance in that section of the cord, and thus a decrease in the inductance of the whole cord. The change in inductance of the cord of present specification has an opposite relation to the stretch in a planar coil where an increased circumference or stretch increases the inductance. Additionally, in embodiments of the present specification, the inductance of the helix is additive. As a result, the cord direction can be looped back on itself and returned to the original starting point while still maintaining its sensitivity to elongation. In case a single loop is used, the helical inductance and a residual loop inductance are in opposite directions, but the helical inductance can be made much larger than the loop to reduce the cancellation. Double helix and dual or doubled-over or out-and-back single helix configurations have currents flowing in both directions which eliminates circumferential loop inductance and so one will not have any cancellation effects from loop inductance. Embodiments of the present specification describe a single helical winding and a double helical winding in RIP cords, but the principles described herein may be extended to any configuration in which induced magnetic fields are generated along the length of a central belt, as opposed to axially along the length of the person being monitored.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

In the description and claims of the application, each of the words "comprise", "include", "have", "contain", and forms thereof, are not necessarily limited to members in a list with which the words may be associated. Thus, they are intended to be equivalent in meaning and be open-ended in that an item or items following any one of these words is not meant to be an exhaustive listing of such item or items, or meant to be limited to only the listed item or items. It should be noted herein that any feature or component described in association with a specific embodiment may be used and implemented with any other embodiment unless clearly indicated otherwise.

It must also be noted that as used herein and in the appended claims, the singular forms "a," "an," and "the" include plural references unless the context dictates otherwise. Although any systems and methods similar or equivalent to those described herein can be used in the practice or testing of embodiments of the present disclosure, the preferred, systems and methods are now described.

The term "helical" refers to a spiral extending through three dimensional space or a curve that repeats, in a circular fashion, its position in two dimensions but is physically displaced along a third dimension. In another embodiment, the term helical refers to a type of smooth space curve with tangent lines at a constant angle to a fixed axis.

In embodiments of the present specification, the terms "helical winding(s)" or "helical form" refers to a coil of wire wound or wrapped helically around a core.

Figure 2:
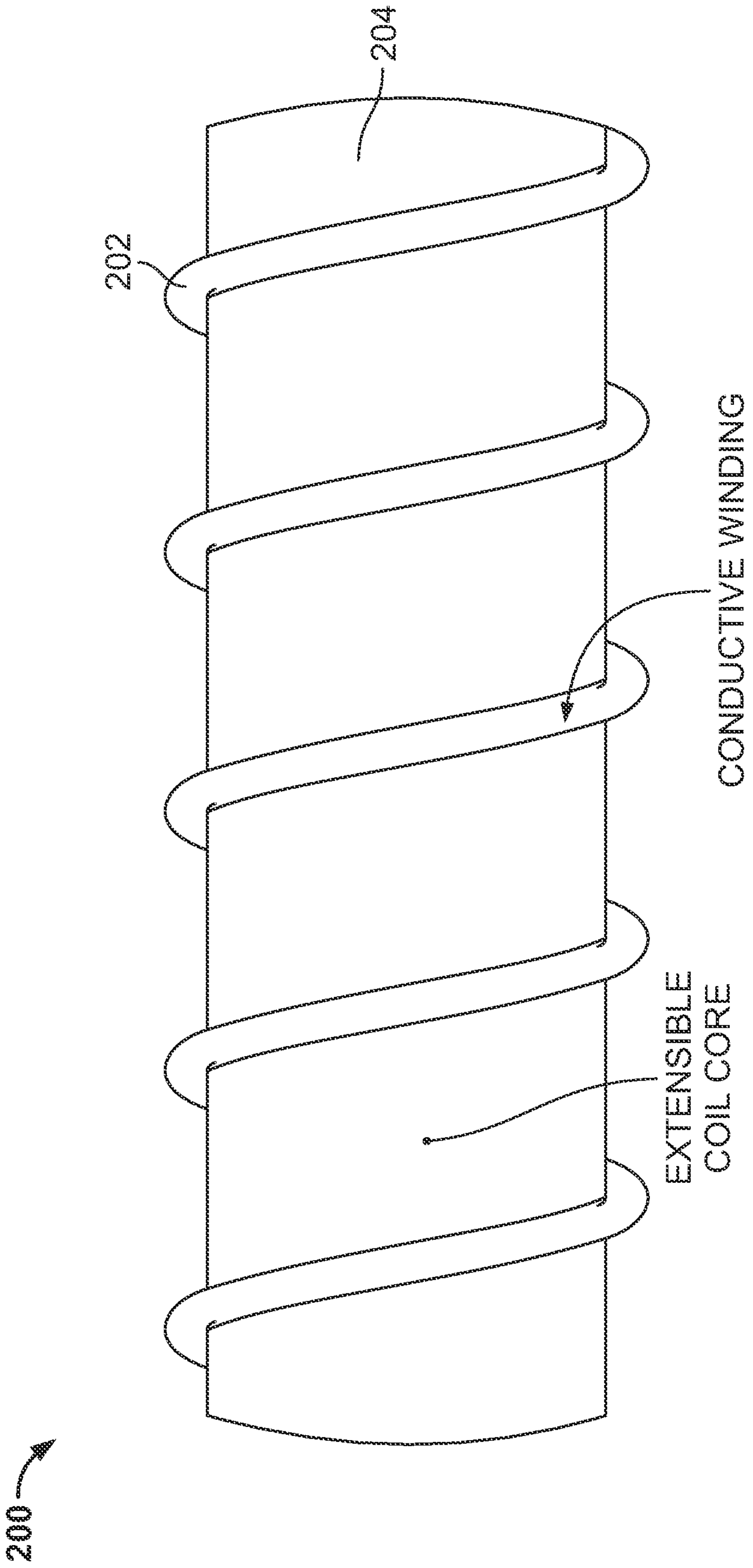
FIG. 2 illustrates a single extensible inductor coil cord for use in a RIP cord, in accordance with some embodiments of the present specification.

FIG. 2 illustrates a single extensible inductor coil cord 200 for use in a RIP cord, in accordance with some embodiments of the present specification. A conductive winding 202 is wound around an elongated cylindrical extensible coil core 204 to form a single helix structure. Coil core 204 is fabricated from an elastic material that enables it to stretch when expanded by pulling, thus allowing for elongation of the entire inductor. In some embodiments, the coil core 204 is made from materials such as, but not limited to, foam, fabric or an elastomer. In some embodiments, the coil core 204 is a cordage comprised of an elastomer such as, but not limited to, spandex, latex, or isoprene, or an equivalent. In embodiments, the coil core 204 comprises multiple strands and may be inside of a woven case. Winding 202 may be made from any type of conductive material such as, but not limited to, copper, steel, stainless steel, metallic fabrics or polymers or braid, beryllium, copper, or magnet wire (coil wire). In embodiments, winding 202 may be made from single or multistrand material. In some embodiments, winding 202 includes an insulation positioned around each winding. Coil core 204 could have a relative permeability near unity or it could be higher like that of iron and various ferrites depending upon the construction of the core. In some embodiments, coil core 204 is made from commonly available elastic cord or cords and have any conceivable cross-sectional shape as long as the coils are normal to an axis along the length of cord 200. In embodiments, the length of cord 200 is defined as a dimension of the cord 200 that extends around the entire periphery of the cord 200. Thus, when the cord 200 is placed around the torso of a user, the length of the cord 200 is the dimension that encircles the user by extending horizontally around a vertical axis of the user, wherein said vertical axis extends from the user's head to the user's feet and is perpendicular to the ground. In embodiments, the elastic cord 200 may be stretched from a first initial length to a second elongated length wherein the second length is at least 1% to 30% greater than the first length and that the direction of stretch is along said length or parallel to the ground when the cord 200 is placed around the torso of a user. In embodiments, the elastic cord 200 may be stretched from a first initial length to a second elongated length wherein the second length is at least 10% greater than the first length and that the direction of stretch is along said length or parallel to the ground when the cord 200 is placed around the torso of a user.

Figure 3B:
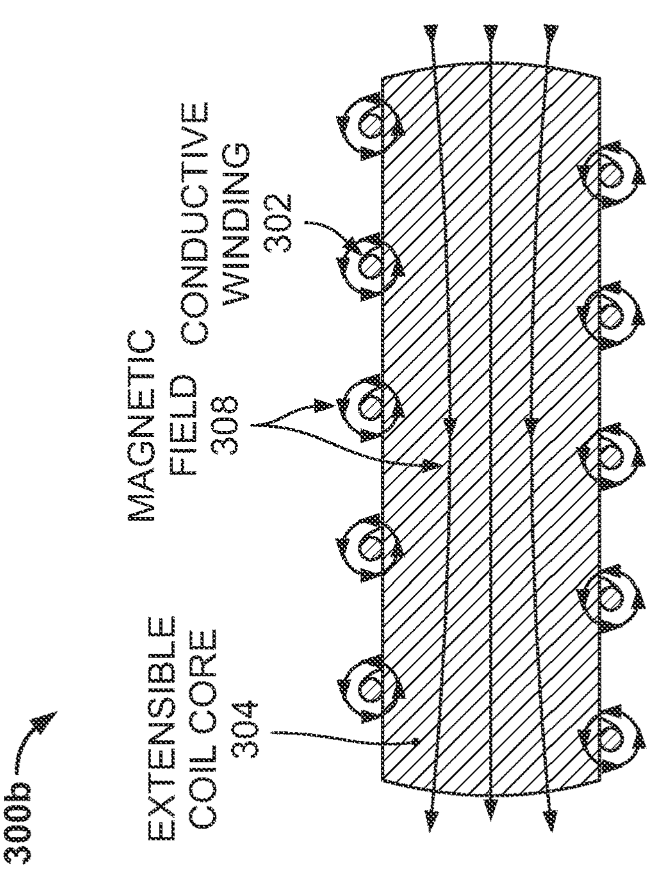
FIG. 3B illustrates a cross-section view, demonstrating positions of the generated magnetic fields, through a central plane in the coil core of FIG. 3A.
Figure 3A:
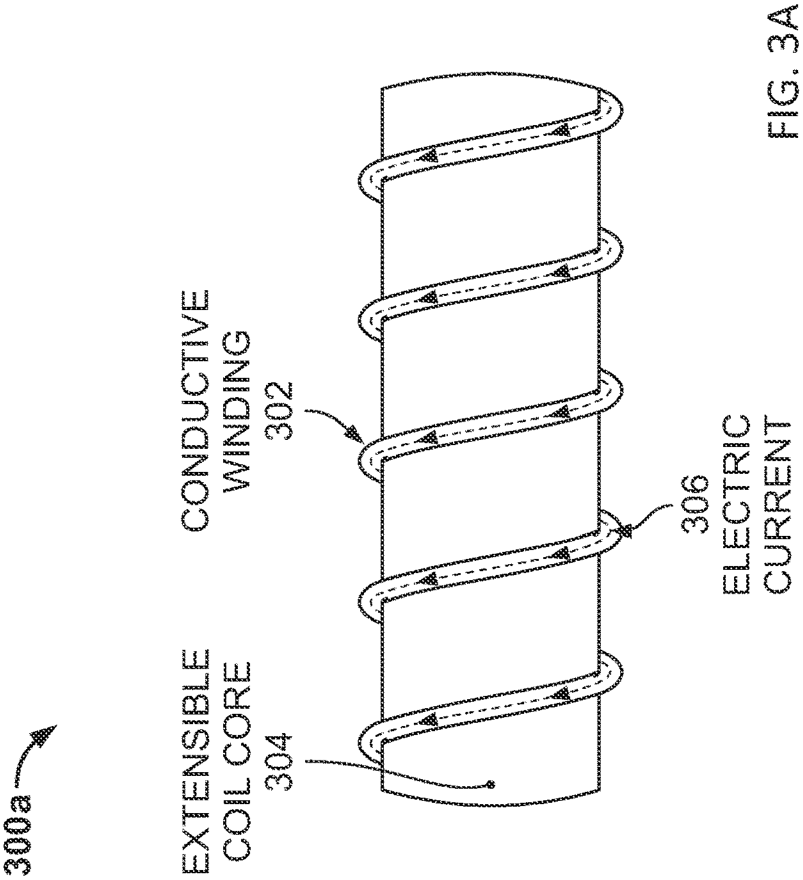
FIG. 3A illustrates electric current flow through a conductive winding of a single extensible inductor coil cord, in accordance with some embodiments of the present specification.

The illustrations of FIGS. 2, 3A and 3B show a round embodiment of cord 200. In different embodiments, cord 200 is integral to other webs or support means including woven webs, extruded components, multi-parts assemblies, an air core, and others. Conductive winding 204 may also be integrated directly with core 204 material and may be disposed inside of a sheath (not shown I FIG. 2) that may be woven, coated or integrated. Conductive winding 204 may also be integrated with a woven fabric that encases the cord or cords 200.

In some embodiments, the coil cord does not include a coil core and may have a conductive winding or coil that is configured to operate as a spring-like material. In such embodiments, the conductive winding may be an air-core coil that is also a spring wherein deflection of the spring would cause a change in inductance of the system just as with an elastic core.

FIG. 3A illustrates electric current 306 flow through a conductive winding 302 of a single extensible inductor coil cord 300*a*, in accordance with some embodiments of the present specification. Conductive winding 302 is wound around an elongated cylindrical extensible coil core 304. FIG. 3B illustrates a cross-section view 300*b* through a central plane of the coil core 304. As shown, a cross section of coil cord 300*b* is orthogonal to the tangent of its circumference. Additionally, view 300*b* shows a magnetic field 308 that is generated by electric current 306 flowing through conductive winding 302. The magnetic field of each loop of a plurality of loops of the winding 302 combines with surrounding fields to create a magnetic field that is along the axis of the extensible inductor coil cord 300*a*, and normal to the plane of winding 302. Embodiments of the present specification provide current flow that produce magnetic fields that are additive. In embodiments, each loop of a plurality of loops of the winding 302 generates a separate magnetic field wherein each of the magnetic fields generated by each of the loops is more additive in intensity than destructive in intensity.

As an alternative to a doubled-over or out-and-back single helix configuration, that is where a single helical winding positioned around an elastic cord is looped around and over itself, the RIP cord can be embodied as a double helical winding. In a double helix configuration, a first helical winding is positioned around the coil core for a desired length, and a second helical winding is wound in the same rotational direction back to the origin. In some embodiments, the conductor for the first and the second helices are one continuous conductive winding. In some embodiments, the conductors for the first and the second helices include separate conductive windings that are electrically connected. Separate conductive windings for the first and second helixes eliminates the need for an elastic belt as a substrate to maintain a geometric separation and allows other mounting configurations to be used for the coil core. For the double helix configuration, the conductive winding(s) for the first and second helices are insulated from one another.

Figure 3D:
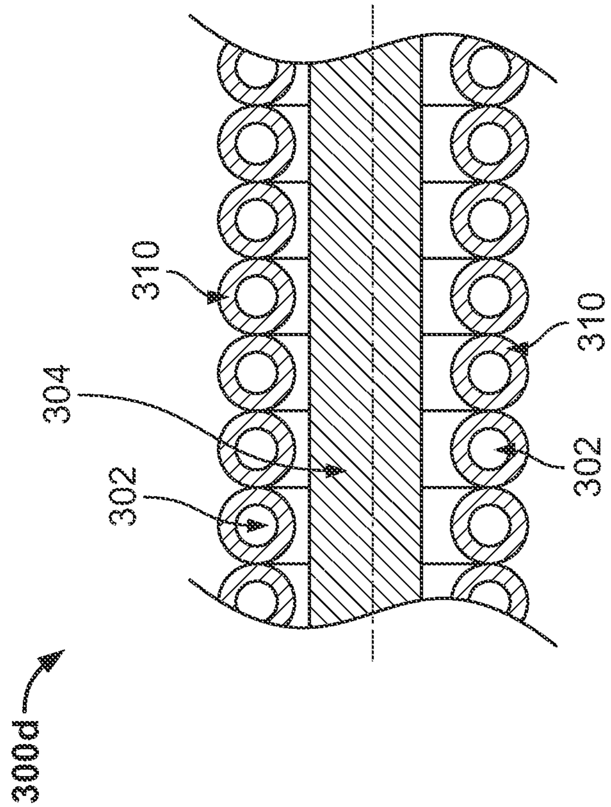
FIG. 3D illustrates a cross-section view of the extensible inductor coil cord of FIG. 3C, in accordance with some embodiments of the present specification.
Figure 3C:
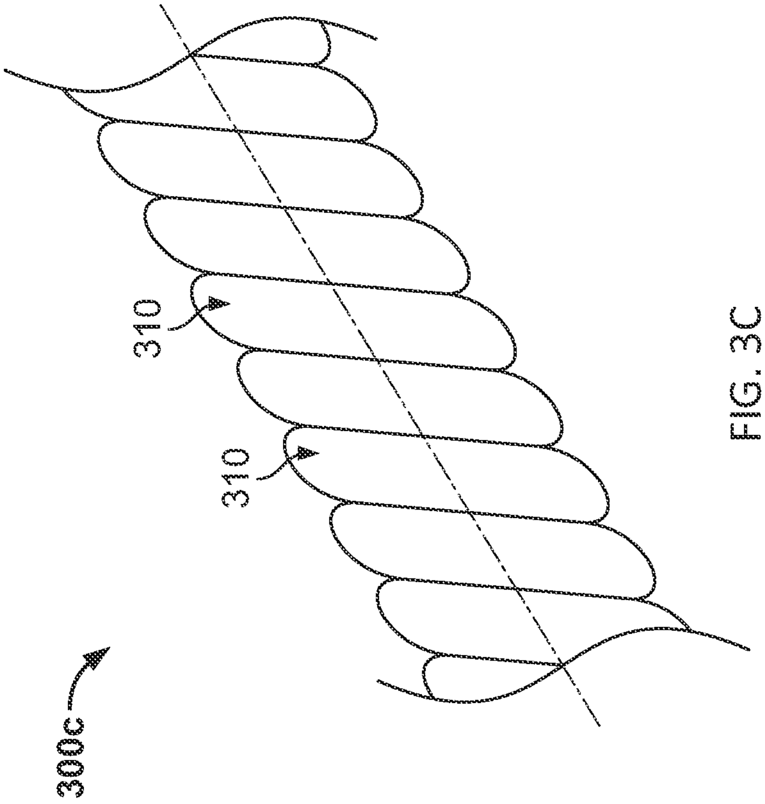
FIG. 3C illustrates an extensible inductor coil cord encased in a plush wrap or casing, in accordance with some embodiments of the present specification.

FIG. 3C illustrates an extensible inductor coil cord 300*c* encased in a plush wrap or casing 310, in accordance with some embodiments of the present specification. In some embodiments, the coil cord 300*c* is representative of any of the inductor coil cord of the present specification (for example, the single extensible inductor coil cord 300*a* of FIG. 3A or the double extensible inductor coil cord 400 of FIG. 4) that is encased in the plush wrap or casing 310. FIG. 3D illustrates a cross-section view 300*d* of the extensible inductor coil cord 300*c*. As shown in FIGS. 3C and 3D, the conductive winding 302 along with the elongated cylindrical extensible coil core 304 are encompassed in the plush wrap or casing 310. The resulting coil cord 300*c* resembles a rope or cable. In embodiments, the plush wrap or casing 310 is made from materials such as, for example, yarn, chenille, foam, or fabric. The plush casing 310 is preferable in uses where there would be direct contact with the skin. In some embodiments, the inductor coil cord 300*c* could also be at the center of a tube-like fabric, or it could have a fabric or cord wrapped around it.

Figure 4:
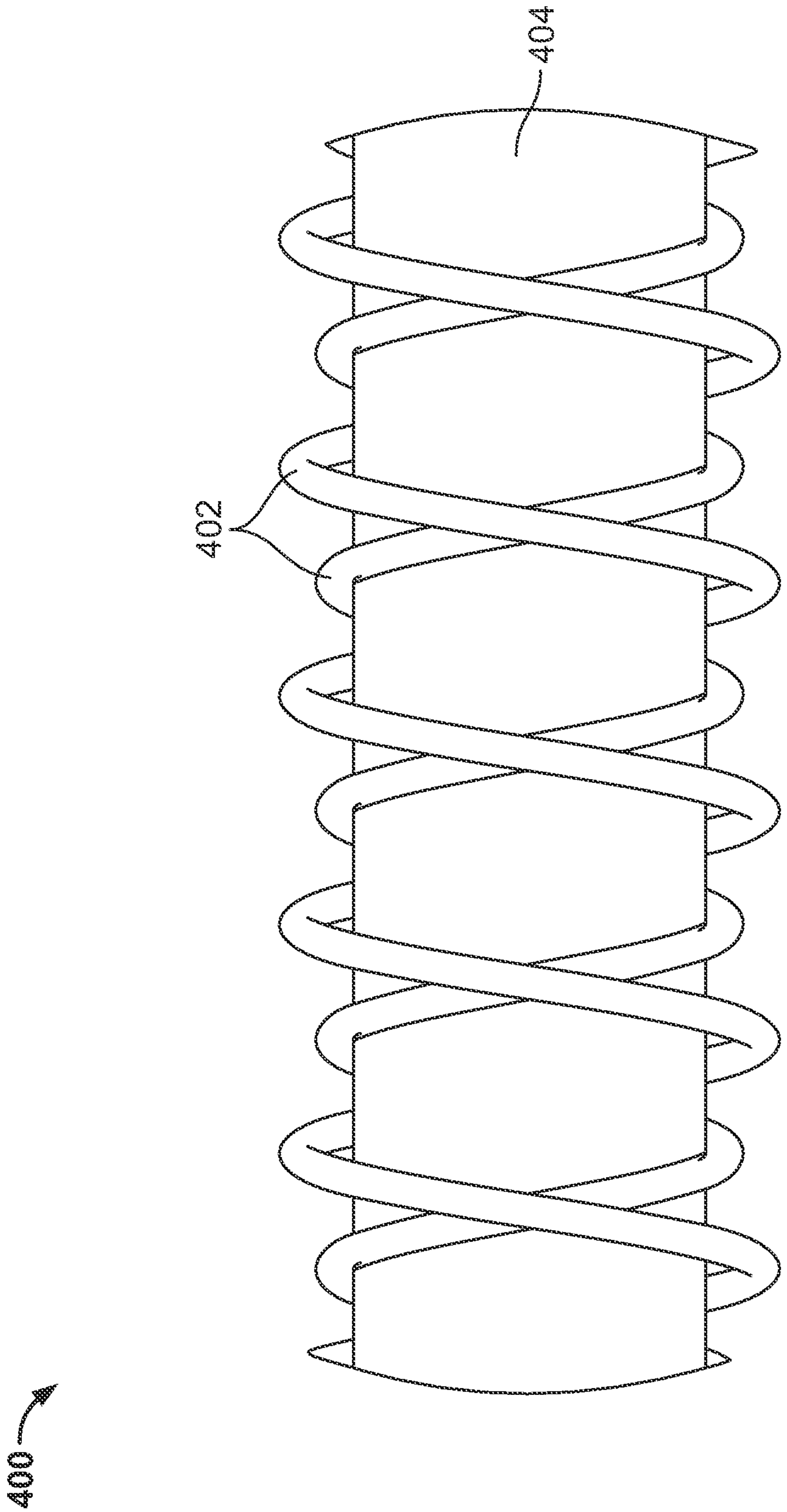
FIG. 4 illustrates a double extensible inductor coil cord for use in a RIP cord, in accordance with some embodiments of the present specification.
Figure 5B:
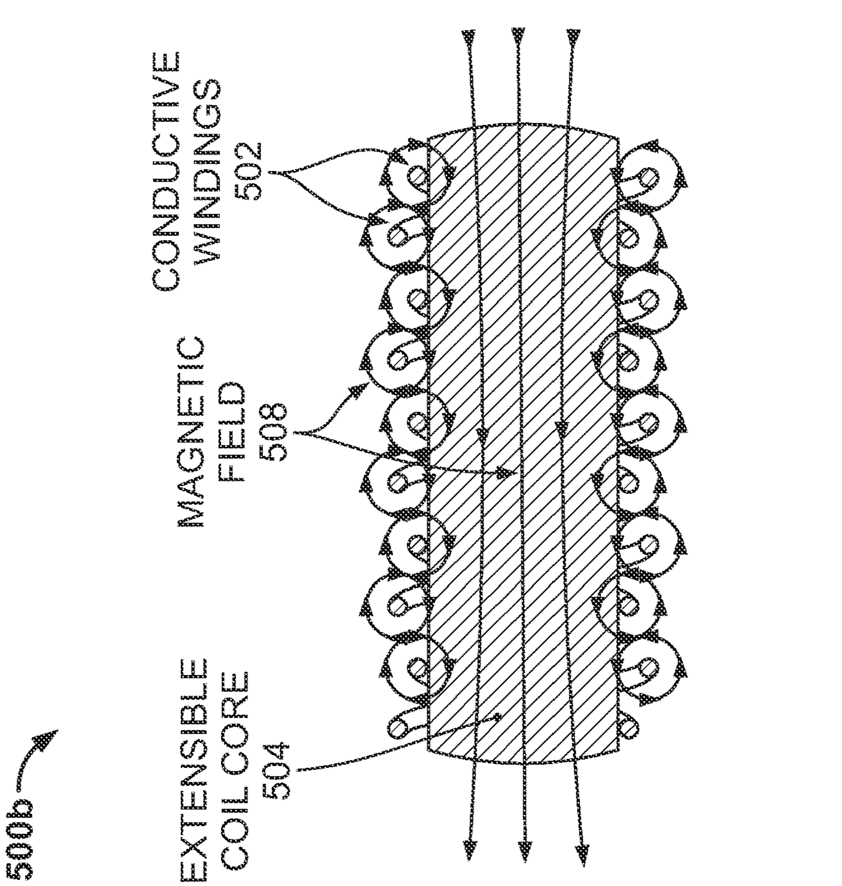
FIG. 5B illustrates a cross-section view, demonstrating positions of the generated magnetic fields, through a central plane in the coil core of FIG. 5A.
Figure 5A:
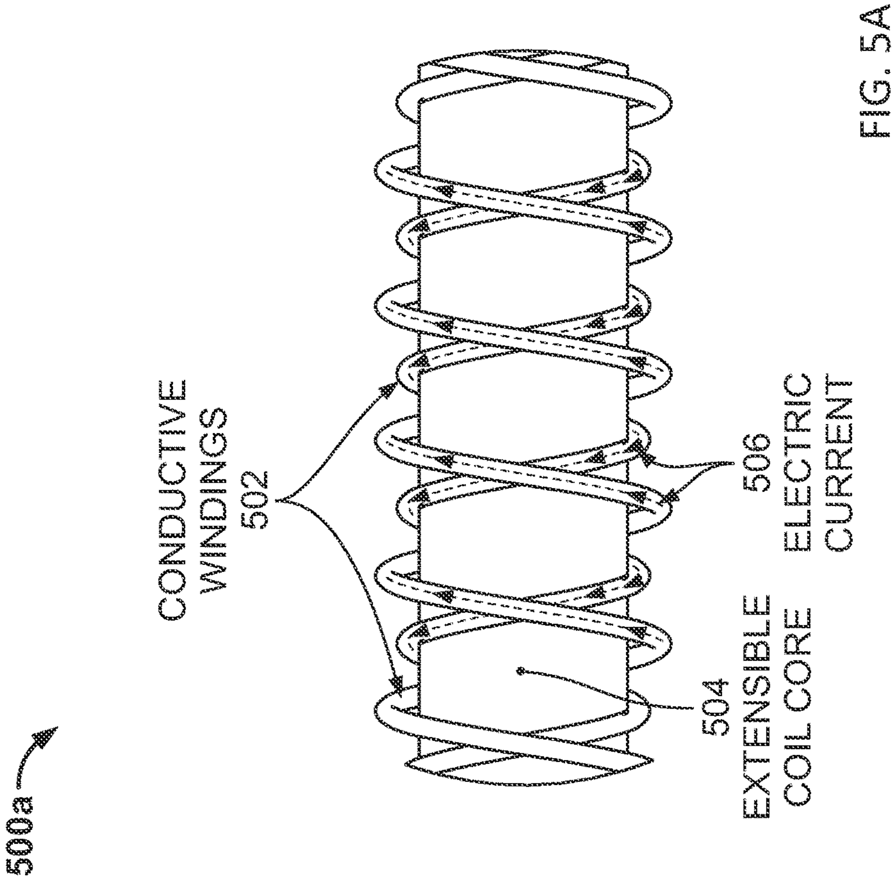
FIG. 5A illustrates electric current flow through conductive windings of a double extensible inductor coil cord, in accordance with some embodiments of the present specification.

FIG. 4 illustrates a double extensible inductor coil cord 400 for use in a RIP cord, in accordance with some embodiments of the present specification. Two conductive windings 402 are wound over an elongated cylindrical extensible coil core 404, in a double helix configuration. Coil core 404 is configured from an elastic material that enables it to stretch when expanded by pulling, thus allowing for elongation of the whole inductor. Windings 402 may be made from any kind of conductive material. In embodiments, windings 402 may be made from single or multistrand material. In some embodiments, windings 402 include an insulation. Coil core 404 could have a relative permeability near unity or it could be higher like that of iron and various ferrites depending upon the construction of the core. In some embodiments, coil core 404 is made from commonly available elastic cord or cords and have any conceivable cross-sectional shape as long as the coils are normal to an axis along the length of cord 400. The illustrations of FIGS. 4, 5A and 5B show a round embodiment of cord 400. In different embodiments, cord 400 is integral to other webs or support means including woven webs, extruded components, multi-parts assemblies, and others. Conductive windings 404 could also be integrated directly with core 404 material and could be disposed inside of a sheath that could be woven or coated or integrated. Conductive windings 404 could also be integrated with a woven fabric that encases a cord or cords 400.

FIG. 5A illustrates electric current 506 flow through conductive windings 502 of a double extensible inductor coil cord 500*a*, in accordance with some embodiments of the present specification. It should be appreciated that the electrical current 506 is generated by the recorder oscillator as previously described. Conductive windings 502 are wound around an elongated cylindrical extensible coil core 504. FIG. 5B illustrates a cross-section view 500*b* through a central plane of the coil core 504. As shown, a cross section of coil cord 500*b* is orthogonal to the tangent of its circumference. Additionally, view 500*b* shows a magnetic field 508 that is generated by electric current 506 flowing through conductive windings 502. The magnetic field for each loop of a plurality of loops of the conductive winding 502 combines with surrounding fields to create a field that extends along the axis of extensible inductor coil cord 500*a*, and normal to the plane of each individual winding 502. In some embodiments, the inductor formed by coil cord 500*a* may not be linear and it can encircle small diameters. In such cases where the inductor encircles small diameters, the instantaneous magnetic field at one planar cross section of coil cord is tangent to the encirclement. Referring again to FIGS. 5A and 5B, current flow of the illustrated inductor coil cord produces magnetic fields that are additive.

Embodiments of FIGS. 2 to 5B illustrate cords where the magnetic fields are along the cord itself. The magnetic fields of embodiments of FIGS. 4, 5A, and 5B are tightly contained. Additionally, as a result of the direction of the magnetic fields, the RIP cords using these embodiments in abdominal and thoracic belts do not interact magnetically, thus simplifying control and physiological monitoring.

An embodiment of a RIP cord coil geometry in accordance with the present specification provides for 10-20 turns per inch on a 0.1 inch elastic coil cord using a wire of scale 30 gauge. In embodiments, different geometries of cord coil are used. In embodiments, the windings are disposed helically about a core so as to provide the intended magnetic field along the core. Therefore, the cross section of the coil is orthogonal to the tangent of the circumference. In another embodiment, the RIP cord coil geometry provides for a range of 10 turn per inch to 50 turns per inch using a wire having a gauge in a range of 10 to 50 and wound around an elastic coil cord having a diameter in a range of 0.01 inch to 4 inches or any suitable range that would achieve the objectives of the present specification.

Figures 6A, 6B, 6C, 6D:
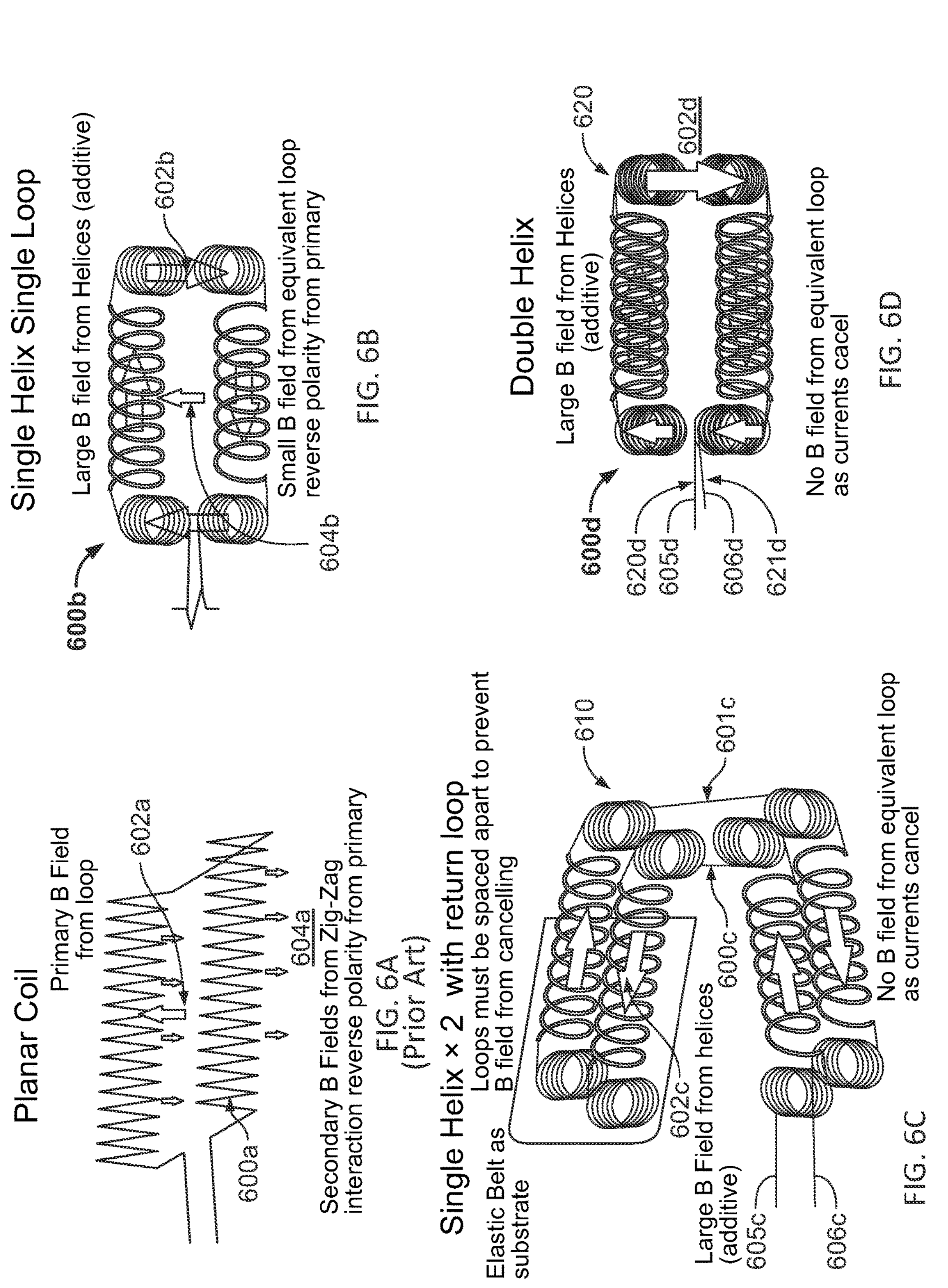
FIG. 6A (Prior Art)
FIG. 6A illustrates a planar wire geometry according to prior art RIP cord coils.
FIG. 6B illustrates magnetic field generated by a loop of a single helix conductive coil, in accordance with an embodiments of the present specification.
FIG. 6C illustrates magnetic field generated by two loops of single helical conductive coils, in accordance with an embodiments of the present specification.
FIG. 6D illustrates magnetic field generated by a loop of a double helix conductive coil, in accordance with an embodiments of the present specification.

As is known, a 'B' field is a magnetic field generated by current moving through a wire and is responsible for inductance. FIG. 6A illustrates a planar coil geometry according to prior art RIP cord coils. FIG. 6A illustrates a magnetic field generated by electric current passed through a planar coil 600*a*. The magnetic field has two components—a primary magnetic field 602*a* from the loop formed by planar coil 600*a*, and secondary magnetic fields 604 from a zig-zag interaction between the various regions of the planar coil 600*a*. Secondary magnetic fields 604 are of reverse polarity from primary magnetic field 602.

FIGS. 6B to 6D illustrate different coil geometries in accordance with embodiments of the present specification. FIG. 6B illustrates a loop of a single helix conductive coil 600*b*. A large primary B 602*b* is formed by electric current passing through various regions of the loop, and a small B 604*b* of reverse polarity from primary B field 602*b* is formed from equivalent loop. Primary B field 602*b* is additive. Though small relative to primary, B field 604*b* is of opposite polarity than B field 602*b*. FIG. 6C illustrates an embodiment of coil geometry including a single helix conductive coil 610 with two conductive coil portions, a first portion 600*c* with a return loop portion 601*c*. In embodiments, the loop is formed such that the coil portions 600*c*, 601*c* are spaced apart to prevent B fields, generated by electric current passing through them, from cancelling. A large additive B field 602*c* is formed by the helices of coil portions 600*c*, 601*c*. Further, as the current directions of each coil of coil portions 600*c*, 601*c* cancel each other, no additional B field is formed from the equivalent loop. FIG. 6D illustrates a double helix coil geometry 600*d*. Electric current passing through the double helix coils 600*d* form a large additive B field 602*d*. Also, no additional B field is formed by the equivalent loop as currents flowing through each coil of coils 600*d* cancel each other.

Figure 8:
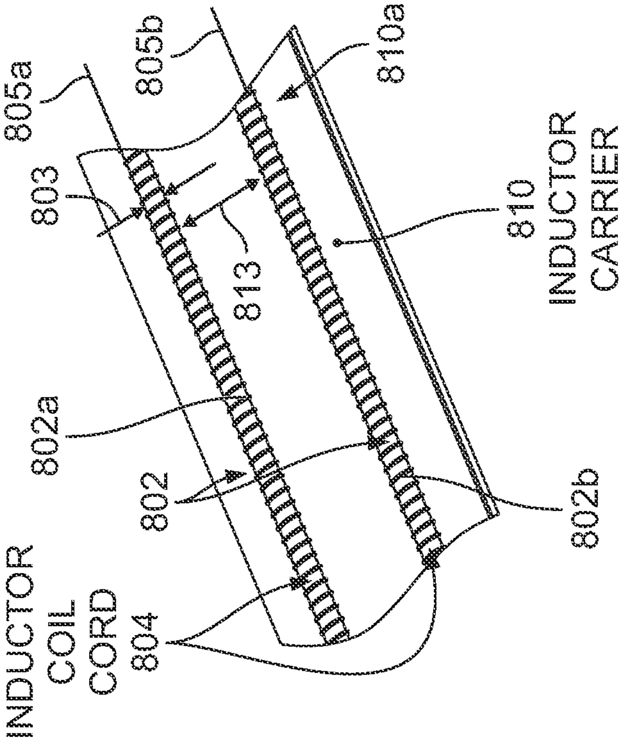
FIG. 8 illustrates an inductor carrier that includes two parallel coil cords, where each cord is wound with a single helical conductive winding, in accordance with some embodiments of the present specification.
Figure 7:
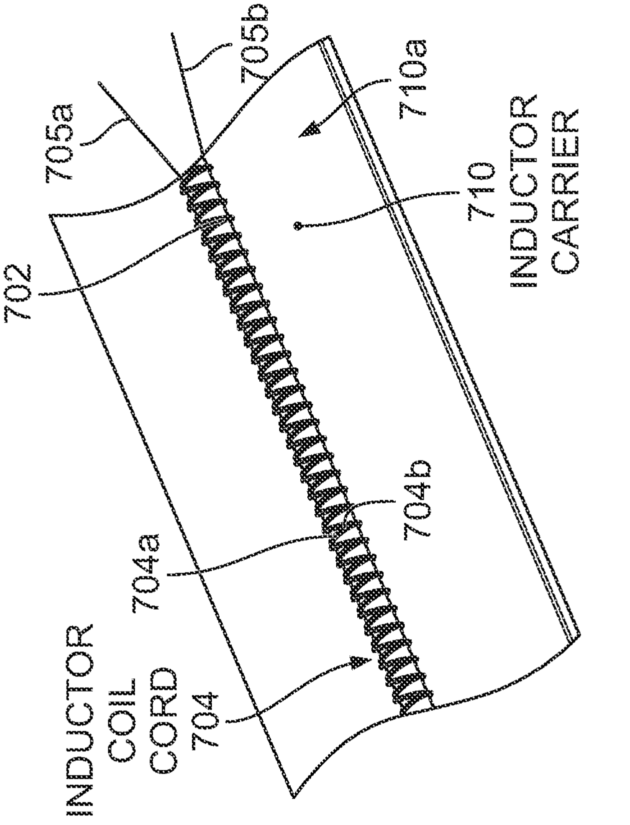
FIG. 7 illustrates an inductor carrier that includes a coil cord wound with a double helix conductive winding, in accordance with some embodiments of the present specification.

FIG. 7 illustrates an inductor carrier 710 that includes a coil cord 704 wound with a double helix conductive winding 702, in accordance with some embodiments of the present specification. FIG. 8 illustrates an inductor carrier 810 that includes two parallel coil portions 802*a*, 802*b*, of a single helix inductor coil cord 804. Each portion 802*a*, 802*b* comprises a looped portion of a wound single helical conductive winding 802, in accordance with some embodiments of the present specification. In some cases, when a doubled-over single helix is used, the parallel portions of the inductor can interact. Therefore, each of the parallel portions 802*a*, 802*b* are spaced several coil diameters 803 apart, creating a separation distance 813, to reduce interaction between them. In preferred embodiments, parallel portions 802*a*, 802*b* are spaced at least 2 coil diameters apart. However, in some embodiments, parallel portions 802*a*, 802*b* could potentially operate with a spacing closer than 2 coil diameters. Inductor carrier 810 is configured with an elastic spacing substrate that maintains the spacing between multiple parallel coil cord portions 802*a*, 802*b*.

Referring to FIGS. 7 and 8 in some embodiments, coil cord 704/804 is disposed into a flat carrier 710/810 to form a web. One or more coil cords 707/804 may be embodied on the web. In case of multiple coil cords 704/804, the cords could be aligned lengthwise or at any other conceivable position to form single, parallel, serpentine, or circuitous paths on the web. In embodiments, coil cord 704/804 is directly integrated or manufactured into the web. Moreover, coil cord 704/804 may be configured of any size. In different embodiments, coil cord 704/804 is located in any region within the plane of the web, such as for example in midplane or towards one of the edges. Stated differently, for the web having a width and a thickness, the coil cord 704/804 may be located in a plurality of different positions with respect to the web. For example, the coil cord 704/804 could be centered in the cross section of the web, on the surface of the web or at the perimeter of the web. The web may be flat, curved, or tubular. In some embodiments, the web is formed around coil cord 704/804.

Embodiments of the present specification provide single or dual helical coil structures to be used with inductor webs that are worn as a belt with the aid of mechanical connection means. In some embodiments, referring simultaneously to FIG. 6C and FIG. 8, a single helical coil structure or winding 610, 802 extends along the carrier or web 810 such that a first portion 600*c*, 802*a* of the coil extends in a first direction along the web and a second portion of the coil 601*c*, 802*b* extends in a second direction, opposite the first direction, along the web to create a 'return loop'. The free end 605*c*, 805*a* of the first portion 600*c*, 802*a* and the free end 606*c*, 805*b* of the second portion 601*c*, 802*b* are each positioned on a first, same end 810*a* of the web 810. Having both free ends 605*c*, 805*a* and 606*c*, 805*b* of the helical coil at one end of the belt allows for attachment of connecting wires during manufacturing. Optionally, in some embodiments, the single helical coil structure or winding 610, 802 is cut proximate a center of its length, creating cut ends. The two cut ends meet each other at a second end of the web, opposite the first end, and are electrically connected via an electrical connector, creating an "out and back" arrangement.

Figure 14A:
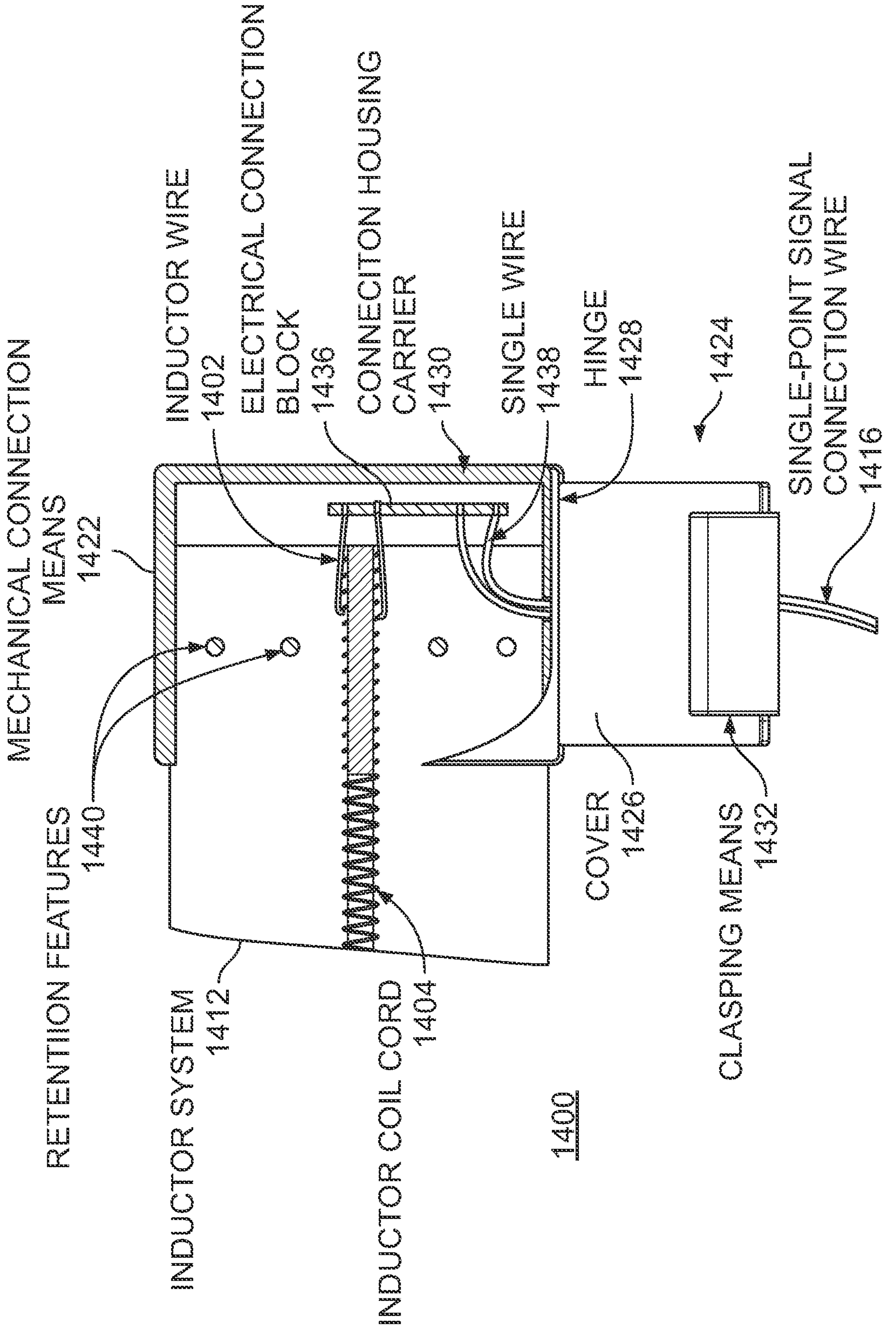
FIG. 14A illustrates another embodiment of a mechanical connection means with an open clasping system, in an inductor encirclement assembly in accordance with some embodiments of the present specification.
Figure 14B:
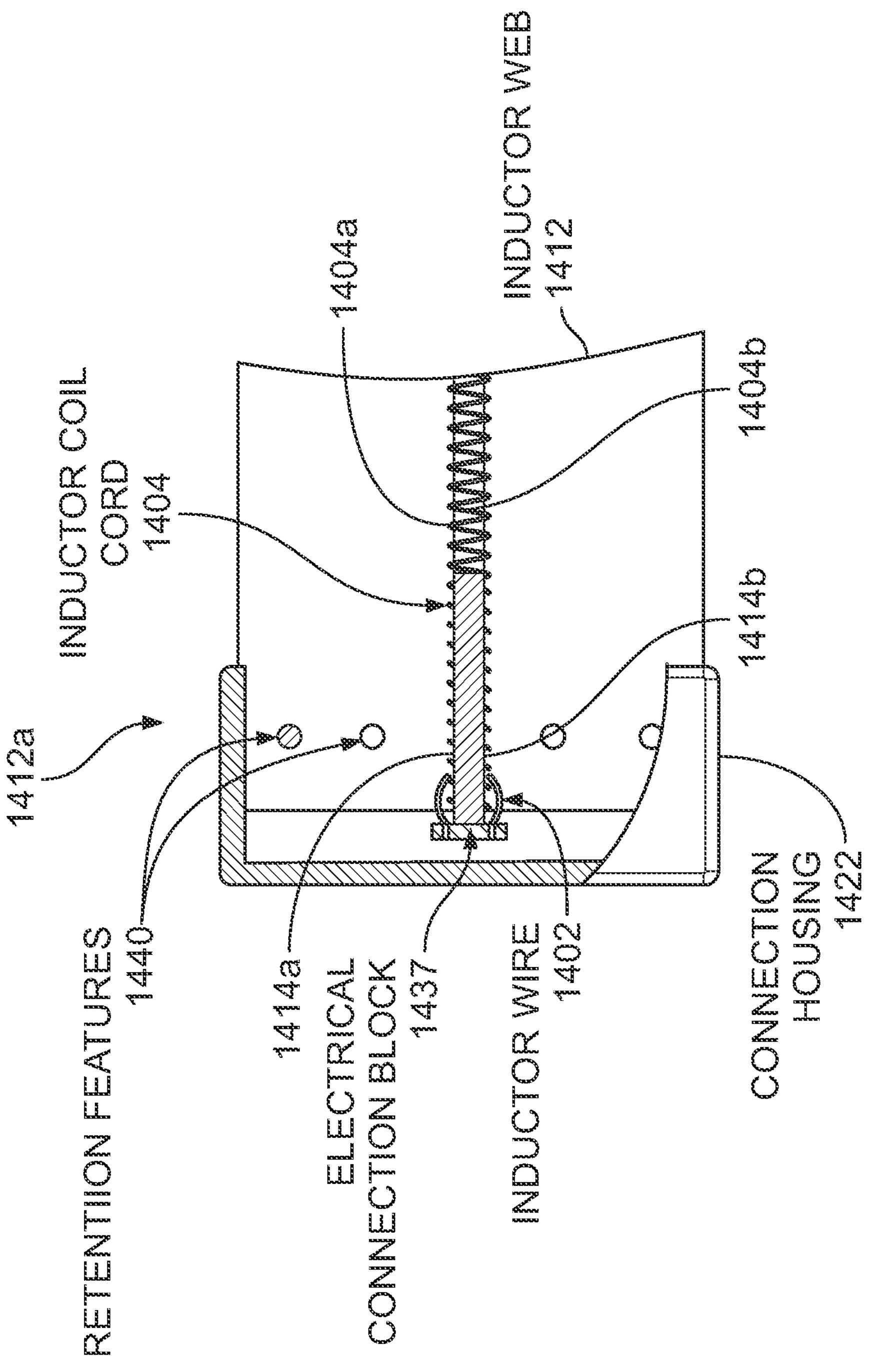
FIG. 14B illustrates the embodiment of mechanical connection means of FIG. 14A without the clasping system, in inductor encirclement assembly in accordance with some embodiments of the present specification.

In other embodiments, referring to FIGS. 6D, 7, and 14B, a dual helical or double helix coil 620, 704, 1404 extends along the carrier or web 710, 1412 such that a first helix 620*d*, 704*a*, 1404*a* of the double helix coil extends in a first direction along the web and a second helix 621*d*, 704*b*, 1404*b* extends in a second direction, opposite the first direction, along the web. The first helix 620*d*, 704*a*, 1404*a* includes a first free end 605*d*, 705*a* and the second helix 621*d*, 704*b*, 1404*b* includes a first free end 606*d*, 705*b*. Each first free end 605*d*, 705*a* and 606*d*, 705*b* is positioned on a first, same end 710*a* of the web 710 and is configured to be electrically connected to a first electrical connection block (1436 in FIG. 14A). In an embodiment, the first helix 620*d*, 704*a*, 1404*a* also includes a second free end 1414*a* and the second helix 621*d*, 704*b*, 1404*b* also includes a second free end 1414*b*. The second free ends 1414*a*, 1414*b* are electrically connected to each other via inductor wires 1402 and second electrical connection block 1437 at a second end 1412*a* of the web 1412. The inductor web is configured to be encircled around a body volume of a user. The belt can be connected to a recorder before attaching to the user, if desired, and a single loop placed around the user and fastened in a number of ways (described below) that are easy to manage. Known electrical connections made by the user are a factor most responsible for failure of accurate measurement of change in inductance. Embodiments of the present specification do not require user-made electrical connections, and thus offer greater reliability and accuracy.

Figure 10A:
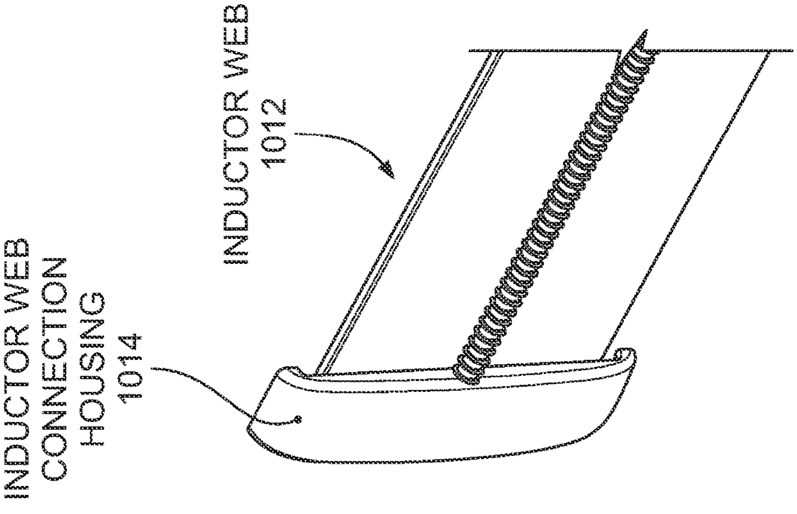
FIG. 10A illustrates an enlarged view of a web connection housing attached to an inductor web, in accordance with some embodiments of the present specification.
Figure 9:
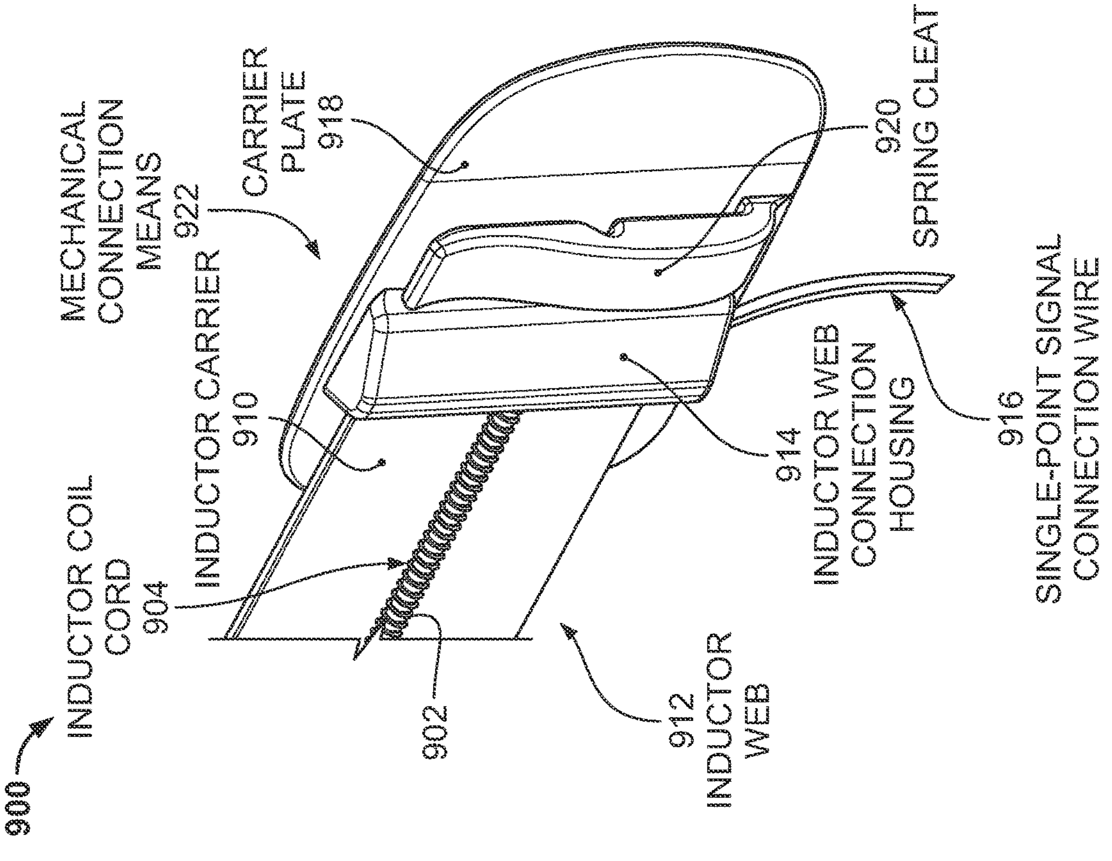
FIG. 9 illustrates an inductor encirclement assembly in accordance with some embodiments of the present specification.

FIG. 9 illustrates an inductor encirclement assembly 900 in accordance with some embodiments of the present specification. An inductor web 912 comprising an inductor coil cord 904 (shown with a double helix conductive coil 902) and an inductor carrier 910 is configured to be placed around a body volume for an RIP application. Inductor web 912 is connected to a connection housing 914 that houses electrical connections and further connects with a single-point electrical wire 916 that connects to a power supply. In embodiments, the electrical wire 916 could include multiple strands or many electrical paths. Also, the term "single-point" means that, on the web 912, there is only one point making an electrical connection to the system. This is in contrast to prior art systems that require electrically conductive buckles or separate electrical connections to the inductor (more than one point). FIG. 10A illustrates an enlarged view of a web connection housing 1014 attached to an inductor web 1012. Referring to FIGS. 9 and 10A, in embodiments, connection housing 914/1014 is configured at a tag end of inductor web 912/1012. In some embodiments, housing 914/1014 is integrated with web 912/1012. In some embodiments, the inductor coil cord 904 is electrically connected without a housing. Referring again to FIG. 9, a carrier plate 918 is configured with a cleat 920 to accept and pin inductor web 912 so that the inductance change of a circumference can be measured. In some embodiments, cleat 920 is a spring cleat. In some embodiments, the carrier plate 918 is made as a single unit, of a plastic, that is bonded to the web 912. The combination of carrier plate 918 with cleat 920 provide a mechanical connection means 922 at a tag end of web 912, to connect housing 914 and inductor web 912, so that assembly 900 encompasses a body volume. The tag end is where inductor web 912 loops to encircle the body volume. In embodiments, assembly 900 could be fabricated as one or could be an assembly of individual parts. Assembly 900 could be made through a variety of manufacturing techniques. In some embodiments, the inductor encirclement assembly of the present specification comprises an extended web which may be required for heavy patients, wherein the inductor coil of the assembly only traverses a part of the inductor web closest to a connection housing comprising connection leads, while the extended web may be used to reach the buckle.

Figure 10B:
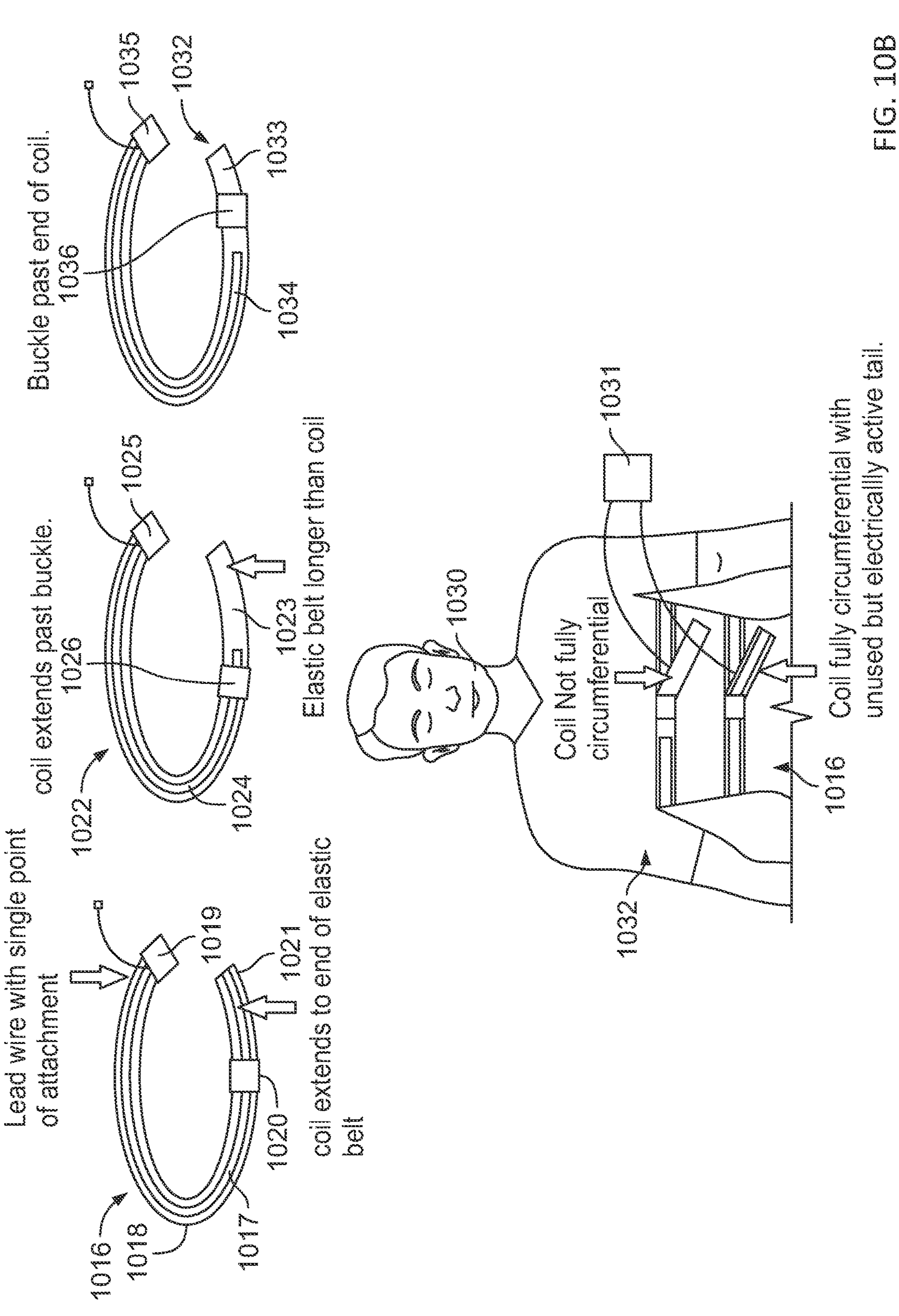
FIG. 10B illustrates alternate configurations of the inductor coil to the inductor web in an inductor encirclement assembly, in accordance with an embodiment of the present specification.

FIG. 10B illustrates alternate configurations of the inductor coil to the inductor web in an inductor encirclement assembly, in accordance with an embodiment of the present specification. Configuration 1016 illustrates a lead wire 1017 which extends to the two ends of an elastic belt 1018, wherein a first end of the belt 1018 comprises connection means 1019 to which the lead wire 1017 connects via a single point of attachment. As can be seen in configuration 1016, the lead wire 1017 extends beyond a buckle 1020 provided proximate a second end of the belt 1018. FIG. 10B also illustrates a patient 1030 wearing the inductor encirclement assembly shown in configuration 1016, wherein the lead wire 1017 extends fully from the first end to the second end of the belt 1018, wherein a tail end 1021 of the belt/wire extending beyond the buckle 1020 is unused but electrically active as the connection means 1019 are connected to an electrical supply 1031.

Configuration 1022 illustrates an elastic belt 1023 which is longer than a lead wire 1024 which extends from a first end of the belt 1023 comprising connection means 1025 to a buckle 1026 provided proximate a second end of the belt 1023. As can be seen in configuration 1022, the lead wire 1024 extends from a first end of the belt 1023 (where said wire is connected to the connection means 1025 via a single point of attachment) to the buckle 1026, and does not extend beyond the buckle 1026.

Configuration 1032 illustrates an elastic belt 1033 which is longer than a lead wire 1034 which extends from a first end of the belt 1033 comprising connection means 1035 to a point before a buckle 1036 provided proximate a second end of the belt 1033. As can be seen in configuration 1032, the lead wire 1034 extends from a first end of the belt 1033 (where said wire is connected to the connection means 1035 via a single point of attachment) to a location on the belt 1033 before the buckle 1036, and does not extends to the buckle 1036. FIG. 10B also illustrates a patient 1030 wearing the inductor encirclement assembly shown in in configuration 1032, wherein the lead wire 1034 extends from a first end of the belt 1033 but does not reach the buckle 1036.

Figure 11A:
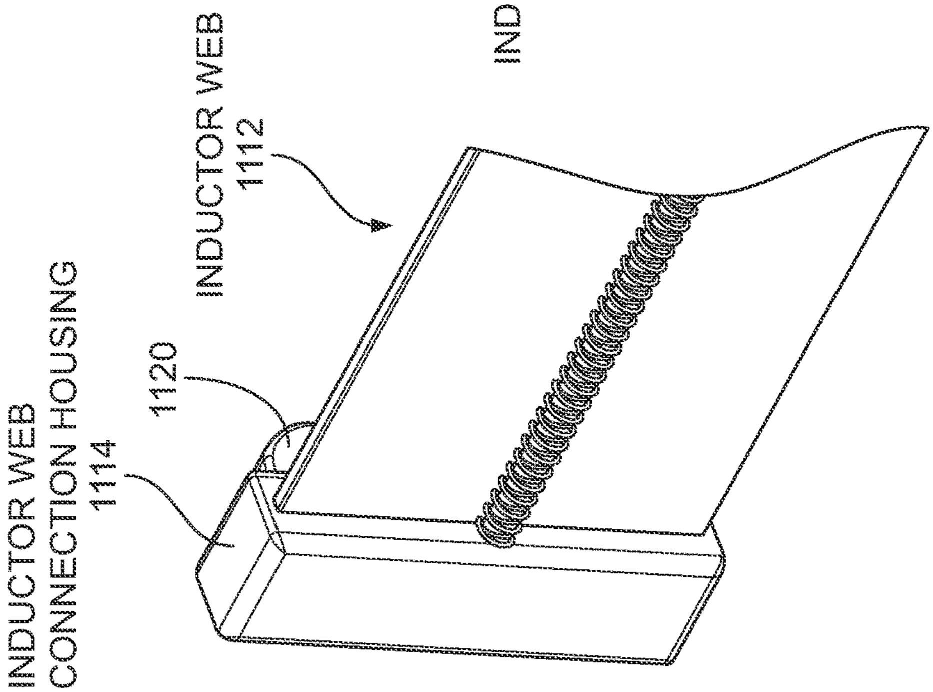
FIG. 11A illustrates a perspective view of housing from an external side of web, in accordance with some embodiments of the present specification.
Figure 11B:
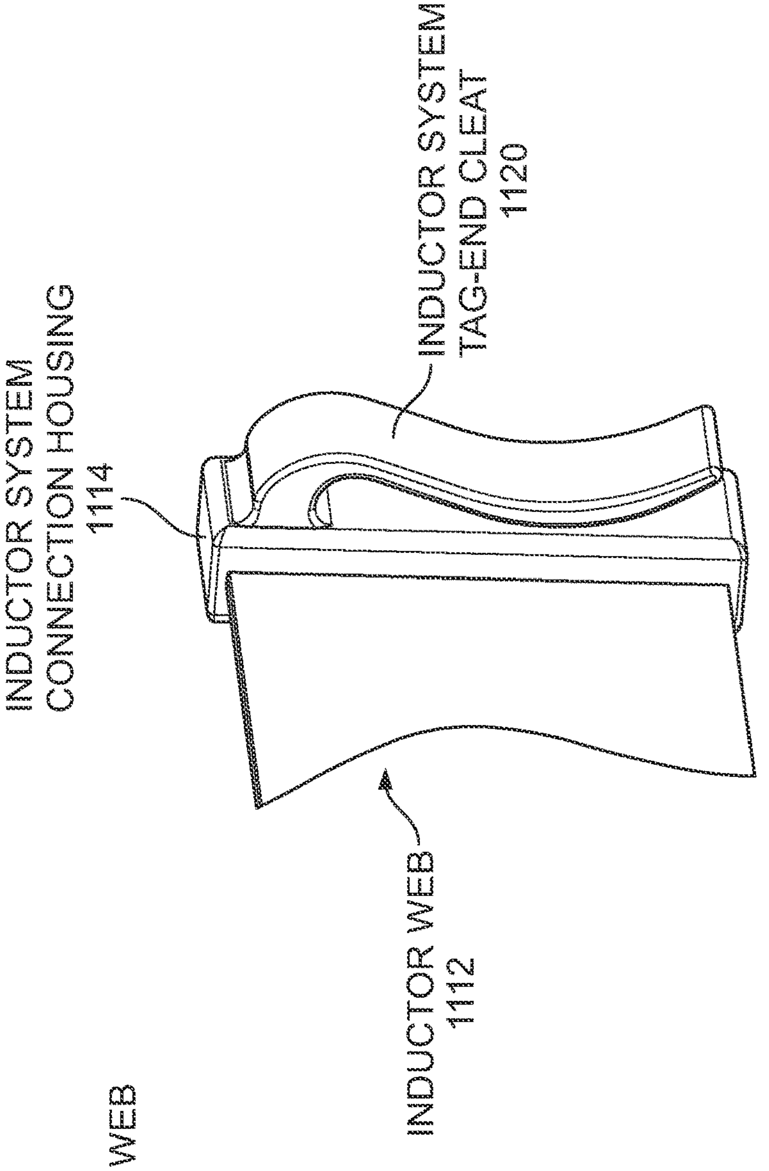
FIG. 11B illustrates a perspective view of housing and a cleat from an internal side of web, in accordance with some embodiments of the present specification.

FIGS. 11A and 11B illustrate another embodiment of an inductor web housing 1114 connected to an inductor web 1112 in accordance with the present specification. FIG. 11A illustrates a perspective view of housing 1114 from an external side of web 1112. FIG. 11B illustrates a perspective view of housing 1114 and a cleat 1120 from an internal side of web 1112. Housing 1114 includes cleat or clip 1120 that is used to retain a tag against encirclement of web 1112 around a body volume. Embodiment of FIG. 11 is used to prevent a free end to the tag of web 1112. While FIG. 9 illustrates an embodiment where housing 914 and cleat 920 are adjacent to each other, and cleat 920 is connected to carrier plate 918, embodiments of FIGS. 11A and 11B illustrate a cleat 1120 attached to a surface of housing 1114. In embodiments, cleat 1120 is configured on an external surface of housing 1114, which is opposite to its internal surface that faces a body volume of a user using inductor web 1112.

Figure 12:
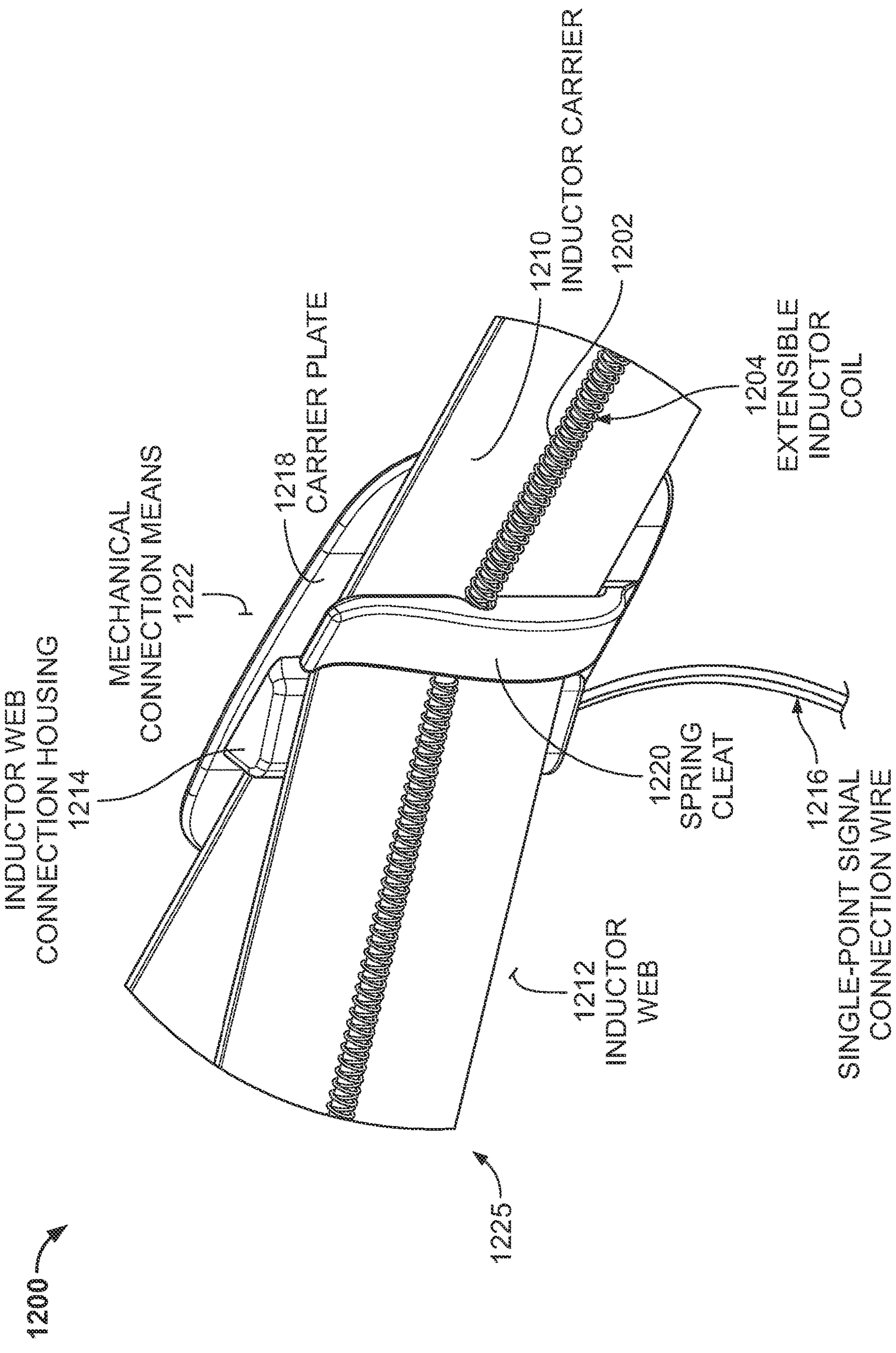
FIG. 12 illustrates an inductor encirclement assembly in accordance with some embodiments of the present specification.

FIG. 12 illustrates an inductor encirclement assembly 1200 in accordance with some embodiments of the present specification. A mechanical connection means 1222 includes a carrier plate 1218 having a shape (such as, but not limited to, flat elongated oval, square, or rectangular) and two surfaces—a first internal surface that faces the body volume of a user while using the assembly 1200, and a second external surface that is opposite to the first surface. The second surface of carrier plate 1218 supports a spring cleat 1220 adjacent to an inductor web connection housing 1214. An inductor web 1212 comprising a conductive coil 1202 that forms a coil cord 1204 on an inductor carrier 1210 encompasses a body volume and loops back so as to be retained by cleat 1220 in position, for use. That is, the inductor web 1212 encircles the user and is cleated to form a belt. The tag 1225 is where inductor web 1212 loops to encircle the body volume. Inductor web 1212 is configured to encircle over a second external surface of connection housing 1214. This arrangement does not require any electrical connection at the mechanical retention means 1222. In accordance with some embodiments, the conductive coil 1202 is a double helix which is stable from the perspective of inductance due to physical manipulation of the tag 1225. This means that the assembly 1200 can have a tag with no ill effect. For example, the tag 1225 may be scrunched, crumpled, or folded with no effect on the system. The spring cleat 1220 is not electrical in nature, and is just meant to retain the belt or web 1212 at a particular circumference corresponding to the user's body volume. In some embodiments, as shown in FIG. 11B, the cleat or clip 1120 on the connection house 1114 is used to retain the tag end 1225. The user is enabled to clip the belt or web 1212 back upon itself. It should be noted that, with the double helix, because of the quality of the inductance, there is no perceptible effect on the system.

Figure 13A:
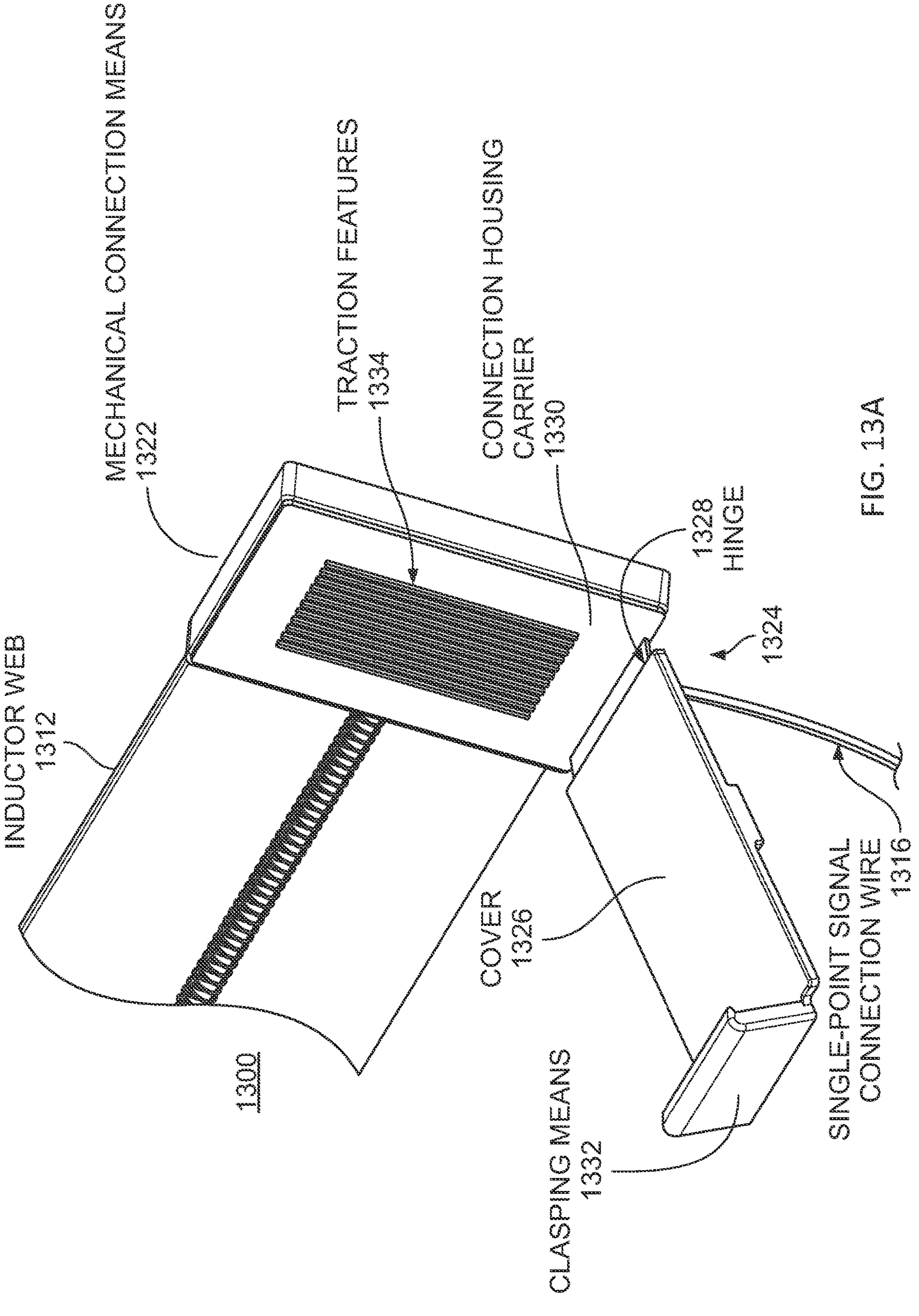
FIG. 13A illustrates another embodiment of a mechanical connection means with an open clasping system, in an inductor encirclement assembly in accordance with some embodiments of the present specification.
Figure 13B:
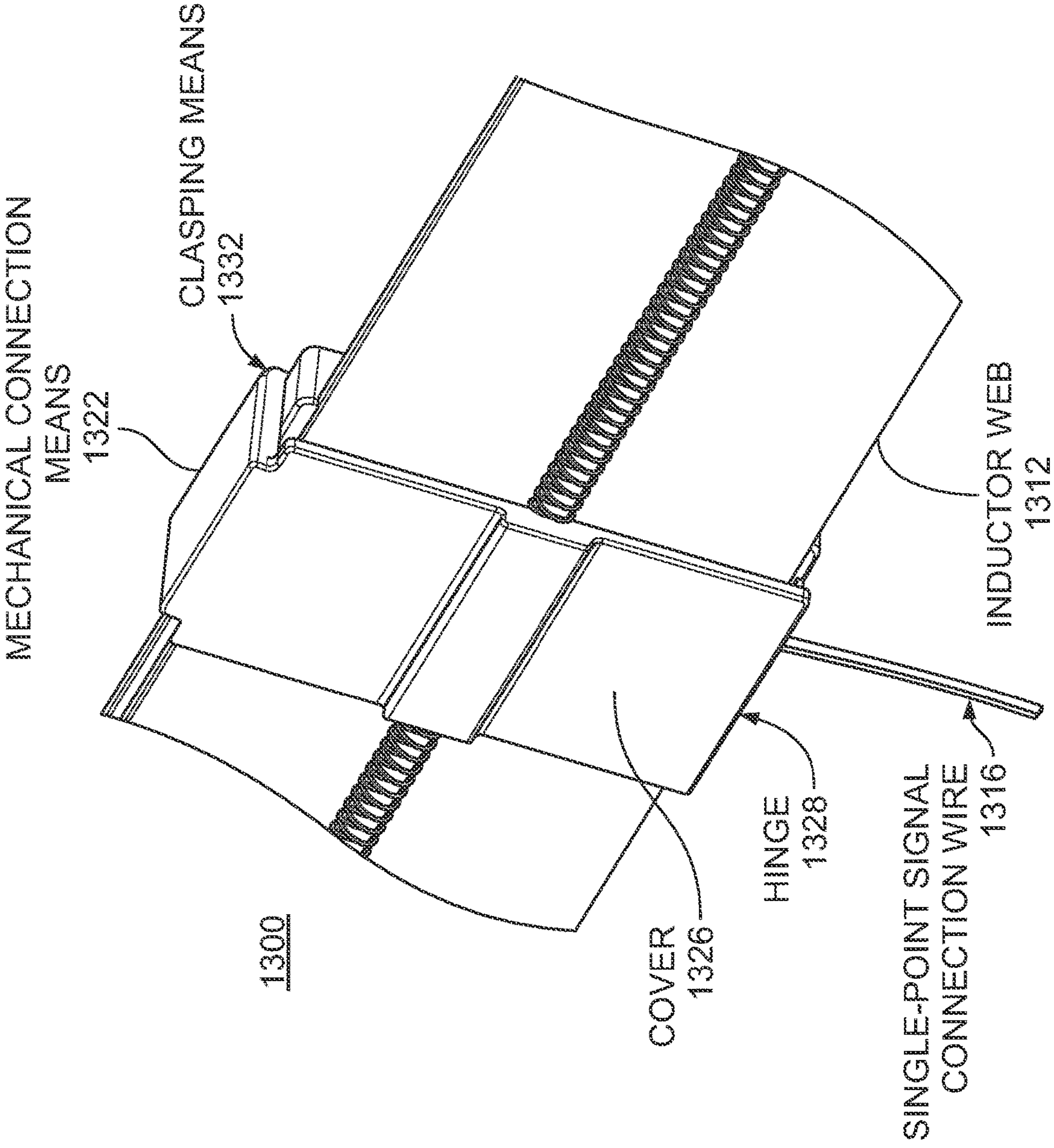
FIG. 13B illustrates the embodiment of mechanical connection means of FIG. 13A with a closed clasping system, in inductor encirclement assembly in accordance with some embodiments of the present specification.

FIG. 13A illustrates another embodiment of a mechanical connection means 1322 with an open clasping system 1324, in an inductor encirclement assembly 1300 in accordance with some embodiments of the present specification. FIG. 13B illustrates the embodiment of mechanical connection means 1322 of FIG. 13A with a closed clasping system 1324, in inductor encirclement assembly 1300 in accordance with some embodiments of the present specification. Mechanical connection means 1322 comprises clasping system 1324. In some embodiments, the clasping system 1324 is rectangular. Clasping system 1324 includes a cover 1326. A first edge of cover 1326 is disposed on a hinge mechanism 1328 and fixed to a connection housing carrier 1330. Cover 1326 rotatably moves around hinge mechanism 1328 to an open position when a second edge, parallel to the first edge, is positioned away from housing carrier 1330; and a closed position when the second edge is positioned proximate to housing carrier 1330. In closed position, cover 1326 covers housing carrier 1330. A clasping means 1332 is configured perpendicular to the rectangular surface of cover 1326 along its second edge. Clasping means 1332 may be any structure or component used to retain cover 1326 against the body or carrier 1330 of the mechanical connection means 1322. In the closed position, clasping means 1332 provides a click lock with housing carrier 1330. An inductor web 1312 attached to a third edge of a rectangular connection housing carrier 1330 may be encircled around a body volume and looped back within housing carrier 1330, where cover 1326 is placed over the encircling inductor web 1312 and locked to a closed position with clasping means 1332, so as to retain the encirclement by inductor web 1312. The third edge extends from a first corner of first edge of housing carrier 1330 to the corresponding corner of second edge of housing carrier 1330, where the first and second edges are parallel. In some embodiments, traction features 1334 are configured on a surface of carrier 1330 of mechanical connection means 1322, to aid in retention of an encircling inductor web 1312. Traction features 1334 comprise convolutions on surface of housing carrier 1330 that could correspond to similar convolutions on a surface of cover 1326 that faces housing carrier 1330 when closed. In embodiments, any variety of hinges 1328 may be used to provide different degrees of freedom and reaction to the forces necessary for closure by cover 1326. In embodiments, connection housing carrier 1330 is coupled to inductor web 1312 through one of a variety of methods including over molding, sonic welding, fasteners, interlocking features, and bonding. Additionally, a single point electrical connection wire 1316 (labelled as 1216 in FIG. 12) extends from a second edge of housing carrier 1330 to connect to a power source.

FIG. 14A illustrates another embodiment of a mechanical connection means 1422 with an open clasping system 1424, in an inductor encirclement assembly 1400 in accordance with some embodiments of the present specification. FIG. 14B illustrates the embodiment of mechanical connection means 1422 of FIG. 14A without the clasping system 1424, in inductor encirclement assembly 1400 in accordance with some embodiments of the present specification. Referring simultaneously to FIGS. 14A and 14B, inductor encirclement assembly includes an inductor web 1412 fitted with an inductor coil cord 1404. One end of inductor web 1412 is attached to a mechanical connection means 1422. Mechanical connection means 1422 includes a connection housing carrier 1430, which in one embodiment, is rectangular in shape. Inductor coil cord 1404 is attached to housing carrier 1430 with inductor wires 1402 that extend from coil cord 1404 to an electrical connection block 1436 located on housing carrier 1430. In some embodiments, a double-helix inductor comprises an 'out and back' configuration, wherein there are two conductive windings electrically connected, effectively creating a single wire. In accordance with some embodiments, the inductor wires 1402 correspond to a conductive winding in a double helix coil. It should be appreciated that the electrical connection block 1436 may also be used to connect two coil cords to their respective connection wire.

Block 1436 is electrically conductive and may be used to produce the various connections needed within connection carrier housing 1430. Block 1436 may operate as a punch down such that conductors could be grasped. The term "punch down" refers to an electrical receptacle that can take a wire, bare or insulated, and not only retain it mechanically but also make an electrical connection. This could require the electrical connection block 1436 to be forced or wedged into position to make an electrical connection. Electrical connection block 1436 electrically connects the inductor wire 1402 to a signal wire 1438 that further extends to connect with a single-point signal connection wire 1416 that emerges from connection housing carrier 1430 to a power source. During use, free end of inductor web 1412 is encircled around a body volume and joined with connection housing carrier 1430 with the aid of one or more retention features 1440. In various embodiments, the one or more retention features 1440 may be protuberances that penetrate the inductor web 1412 and retain the assembly 1400 in place. The one or more retention features may include, for example, screws, over-molding, hooks, teeth, plastic protuberances, resin bonding, or glue. Retention features 1440 may penetrate inductor web 1412 to provide interlocking. Mechanical connection means 1422 comprises clasping system 1424. In some embodiments, the clasping system 1424 is rectangular and corresponds to the structure of connection housing carrier 1430. Clasping system 1424 includes a cover 1426. A first edge of cover 1426 is disposed on a hinge mechanism 1428 and fixed to connection housing carrier 1430. Cover 1426 rotatably moves along hinge mechanism 1428 to an open position when a second edge, parallel to the first edge, is positioned away from housing carrier 1430 and a closed position when the second edge is positioned proximate to housing carrier 1430. In closed position, cover 1426 covers housing carrier 1430. A clasping means 1432 is configured perpendicular to the rectangular surface of cover 1426 along its second edge. Clasping means 1432 may be any structure or component used to retain cover 1426 against the body or carrier 1430 of the mechanical connection means 1422. In the closed position, clasping means 1432 provides a click lock with housing carrier 1430.

In embodiments, mechanical connection means 1422 is assembled from more than one part. Assembly, bonding, or a combination of both is used to capture components that form retention features 1440, electrical connection block 1436, or any other component. Further, in embodiments, connection housing carrier 1430 contains voids or chambers to be potted or filled with resins, compounds, or plastic.

Different embodiments of the present specification include variations of coil cord configurations. In embodiments, the coil cord is made from ferromagnetic material. In some embodiments, some segments of the coil cord are stretchable, and some segments are non-stretchable. In some embodiments, stretchable and not stretchable segments include portions where a ferromagnetic material is pulled in and out from the helical windings of the coil cord. In some embodiments, coil cords may use more than two layers of helical wrapping of conductive windings, to form a multi-helix coil cord. In some embodiments, single helix configurations include more than two loops of single helix cording in RIP belts. Some embodiments of the present specification provide conductive winding arrangements where the spacing between each winding of the helical coil is not uniform. Some embodiments provide conductive winding arrangements where the helical coil rotation direction is reversed one or more times along the cord. In some embodiments, coil cords include sticky tabs at periodic lengths that enable the cord to stick to a body volume of a user. An exemplary periodic length is of 8 inches and may vary from 0.25 inches to 20 inches. Alternatively, the entire length of a coil cord may have a sticky material to bond the cord or belt to the user. In embodiments, an RIP belt configured using the coil cord embodiments of the present specification includes electrical connectors that are away from either ends of the belt wherein the ends are not engaged in an extension cycle. Stated differently, electrical connectors may be placed anywhere on the RIP belt.

Although the present specification has been described with particular focus on an RIP device for measuring respiratory effort of a patient, the present specification is also designed for a wide range of applications where a length or circumference signal or measurement is needed for any physically reasonable item or subject. The above examples are merely illustrative of the many applications of the system of present specification. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

What is claimed is:

1. A respiratory monitoring system, comprising:

a cord configured to extend around a torso of a person, wherein the cord comprises:

a core member comprising an elastic material, wherein the core member is defined by a length and wherein the elastic material is configured to stretch from a first length to a second length, when a force is applied thereto and;

a first helical conductive coil positioned around the core member, wherein the first helical conductive coil is adapted to generate a magnetic field substantially aligned with and extending along a longitudinal axis of the core member such that the magnetic field extends circumferentially around the torso when worn and is not oriented normal to the torso surface when electric current having a predefined frequency is passed through the first helical conductive coil; and a second helical conductive coil positioned parallel to the first helical conductive coil, coiled in a direction opposite to a coil direction of the first helical conductive coil, and wrapped around the core member wherein magnetic fields generated by the first and second helical conductive coils are configured to combine additively along the longitudinal axis of the core member and wherein the system is configured such that magnetic field interaction between overlapping portions of the cord or between multiple cords is reduced or non-destructive;

an electrical current source in electrical communication with the first helical conductive coil and adapted to generate said electric current;

a sensor electrically coupled to the first helical conductive coil and configured to measure a change in at least one of an inductance of the first helical conductive coil or the frequency of electrical current in the first helical conductive coil; and a controller coupled to the sensor and configured to receive data indicative of said measured change and determine a respiration value based on said data.

2. The respiratory monitoring system of claim 1 wherein the second length is at least 10% greater than the first length.

3. The respiratory monitoring system of claim 1, wherein the second helical conductive coil is electrically insulated from the first helical conductive coil.

4. The respiratory monitoring system of claim 1, wherein a first magnetic field generated by a first loop of the first helical conductive coil and a second magnetic field generated by a second loop of the first helical conductive coil are more additive in intensity than destructive in intensity.

5. The respiratory monitoring system of claim 1, wherein the first helical conductive coil is wrapped in a casing configured to prevent a surface of the first helical conductive coil from directly contacting a user's skin.

6. The respiratory monitoring system of claim 1, wherein the first helical conductive coil comprises windings having a density in a range of 10 to 20 turns per inch and wherein the first helical conductive coil comprises a wire in a range of 20 to 40 gauge.

7. The respiratory monitoring system of claim 1, wherein the first helical conductive coil comprises windings having a density in a range of 1 turn per inch to 50 turns per inch using a wire having a gauge in a range of 10 to 50 and wherein the core member has a diameter in a range of 0.01 inch to 4 inches.

8. The respiratory monitoring system of claim 1, wherein the cord is disposed on a flat carrier to form a web.

9. The respiratory monitoring system of claim 8, wherein the web comprises a second cord and wherein the second cord comprises a third helical conductive coil wound around a second core member, and wherein the third helical conductive coil is adapted to generate a magnetic field extending along a length of the second core member when electric current having a predefined frequency is passed through the third helical conductive coil.

10. The respiratory monitoring system of claim 8, wherein the web is shaped as a flat, curved, or tubular surface.

11. The respiratory monitoring system of claim 8, wherein the cord is centered in a cross section of the web, positioned on an exterior surface of the web or positioned in a perimeter of the web.

12. The respiratory monitoring system of claim 8, wherein the web comprises a connector that mechanically connects a first end of the web to a second end of the web when the web is encircled around the torso.

13. The respiratory monitoring system of claim 1 wherein a first portion of the cord extends along one direction on the core member and a second portion of the cord extends along a second opposing direction on the core member creating a return loop, and wherein a free end of the first and the second portions are aligned at a same end of the core member.

14. The respiratory monitoring system of claim 1, wherein the electrical current source comprises an oscillator configured to generate the electric current having the predefined frequency.

15. A method of monitoring a respiration rate of a person, comprising:

positioning a respiratory inductance plethysmography belt around a torso of a person wherein the respiratory inductance plethysmography belt comprises: a carrier having a cord positioned thereon, wherein the cord comprises a core member made of an elastic material, wherein the core member is defined by a length and wherein the elastic material is configured to stretch from a first length to a second length in a direction parallel to a ground level when the person is standing and when a force is applied thereto, a first helical conductive coil positioned around the core member, wherein the first helical conductive coil is adapted to generate a magnetic field substantially aligned with and extending along a longitudinal axis of the core member such that the magnetic field extends circumferentially around the torso when worn and is not oriented normal to the torso surface when electric current having a predefined frequency is passed through the first helical conductive coil, and a second helical conductive coil positioned parallel to the first helical conductive coil, coiled in a direction opposite to a coil direction of the first helical conductive coil, and wrapped around the core member, wherein magnetic fields generated by the first and second helical conductive coils are configured to combine additively along the longitudinal axis of the core member and wherein the cord is configured such that magnetic field interaction between overlapping portions of the cord or between multiple cords is reduced or non-destructive;

activating an electrical current source in electrical communication with the first helical conductive coil to generate said electric current;

activating a sensor electrically coupled to the first helical conductive coil;

using the sensor, measuring a change in at least one of an inductance of the first helical conductive coil or the frequency of electrical current in the first helical conductive coil; and determining a respiration value based on the measured change in the inductance or the frequency.

16. The method of claim 15, wherein the second helical conductive coil is electrically insulated from the first helical conductive coil.

17. The method of claim 15, wherein the first helical conductive coil comprises windings having a density in a range of 10 to 20 turns per inch and wherein the first helical conductive coil comprises a wire in a range of 20 to 40 gauge.

18. The method of claim 15, wherein the carrier comprises a second extensible cord and wherein the second extensible cord comprises a third helical conductive coil wound around a second core member and wherein the third helical conductive coil is adapted to generate a magnetic field extending along a length of the second core member when electric current having a predefined frequency is passed through the third helical conductive coil.

19. The method of claim 15, wherein the carrier comprises a web having a mechanical connector that connects a first end of the web to a second end of the web when the web is encircled around the torso.

20. The method of claim 15, wherein the electrical current source comprises an oscillator configured to generate the electric current having the predefined frequency.

* * * * *